(12) United States Patent
Hull et al.

(10) Patent No.: US 7,139,598 B2
(45) Date of Patent: Nov. 21, 2006

(54) DETERMINATION OF A MEASURE OF A GLYCATION END-PRODUCT OR DISEASE STATE USING TISSUE FLUORESCENCE

(75) Inventors: Edward L. Hull, Fairport, NY (US); Marwood Neal Ediger, Albuquerque, NM (US); Christopher D. Brown, Albuquerque, NM (US); John D. Maynard, Albuquerque, NM (US); Robert D. Johnson, Albuquerque, NM (US)

(73) Assignee: Veralight, Inc., Albuquerque, NM (US)

( * ) Notice: Subject to any disclaimer, the term of this patent is extended or adjusted under 35 U.S.C. 154(b) by 0 days.

(21) Appl. No.: 10/972,173

(22) Filed: Oct. 22, 2004

(65) Prior Publication Data

US 2005/0148834 A1 Jul. 7, 2005

Related U.S. Application Data

(63) Continuation-in-part of application No. 10/116,272, filed on Apr. 4, 2002.

(60) Provisional application No. 60/517,418, filed on Nov. 14, 2003, provisional application No. 60/515,343, filed on Oct. 28, 2003.

(51) Int. Cl.
*A61B 5/00* (2006.01)
(52) U.S. Cl. .................. 600/317; 600/310; 600/476
(58) Field of Classification Search ........ 600/309–310, 600/322, 476, 473
See application file for complete search history.

(56) References Cited

U.S. PATENT DOCUMENTS 5,582,168 A 12/1996 Samuels et al. ............ 128/633

(Continued)

FOREIGN PATENT DOCUMENTS

WO WO 01/22869 A1 4/2001

OTHER PUBLICATIONS

*Economic Costs of Diabetes in the U.S. in 2002*, American Diabetes Association, Diabetes Care, vol. 26, No. 3, Mar. 2003.

(Continued)

*Primary Examiner*—Eric F. Winakur
(74) *Attorney, Agent, or Firm*—V. Gerald Grafe

(57) ABSTRACT

A method of determining a measure of a tissue state (e.g., glycation end-product or disease state) in an individual. A portion of the tissue of the individual is illuminated with excitation light, then light emitted by the tissue due to fluorescence of a chemical with the tissue responsive to the excitation light is detected. The detected light can be combined with a model relating fluorescence with a measure of tissue state to determine a tissue state. The invention can comprise single wavelength excitation light, scanning of excitation light (illuminating the tissue at a plurality of wavelengths), detection at a single wavelength, scanning of detection wavelengths (detecting emitted light at a plurality of wavelengths), and combinations thereof. The invention also can comprise correction techniques that reduce determination errors due to detection of light other than that from fluorescence of a chemical in the tissue. For example, the reflectance of the tissue can lead to errors if appropriate correction is not employed. The invention can also comprise a variety of models relating fluorescence to a measure of tissue state, including a variety of methods for generating such models. Other biologic information can be used in combination with the fluorescence properties to aid in the determination of a measure of tissue state. The invention also comprises apparatuses suitable for carrying out the method, including appropriate light sources, detectors, and models (for example, implemented on computers) used to relate detected fluorescence and a measure of tissue state.

44 Claims, 19 Drawing Sheets

U.S. PATENT DOCUMENTS

| | | | | |
|---|---|---|---|---|
| 5,601,079 | A | | 2/1997 | Wong et al. ............... 128/633 |
| 5,725,480 | A | * | 3/1998 | Oosta et al. ............... 600/310 |
| 6,070,093 | A | * | 5/2000 | Oosta et al. ............... 600/316 |
| 6,088,606 | A | | 7/2000 | Ignotz et al. ............... 600/316 |
| 6,124,597 | A | * | 9/2000 | Shehada et al. ............ 600/323 |
| 6,201,989 | B1 | * | 3/2001 | Whitehead et al. ......... 600/476 |
| 6,505,059 | B1 | | 1/2003 | Kollias et al. ............... 600/316 |
| 6,571,118 | B1 | | 5/2003 | Utzinger et al. ............ 600/476 |
| 2002/0016534 | A1 | * | 2/2002 | Trepagnier et al. ......... 600/316 |
| 2003/0013973 | A1 | | 1/2003 | Georgakoudi et al. ...... 600/473 |
| 2004/0064053 | A1 | * | 4/2004 | Chang et al. ............... 600/478 |
| 2004/0068193 | A1 | * | 4/2004 | Barnes et al. ............... 600/476 |

OTHER PUBLICATIONS

*Report of the Expert Committee on the Diagnosis and Classification of Diabetes Mellitus,* The Expert Committee on the Diagnosis and Classification of Diabetes Mellitus, Diabetes Care, vol. 26, Supplement 1, Jan. 2003.

*The Effect of Intensive Treatment of Diabetes on the Development and Progression of Long-Term Complications in Insulin-Dependent Diabetes Mellitus,* The Diabetes Control and Complications Trial Research Group, The New England Journal of Medicine, vol. 329:977-986, No. 14, Sep. 30, 1993.

*Reduction in the Incidence of Type 2 Diabetes with Lifestyle Intervention or Metformin,* Diabetes Prevention Program Research Group, The New England Journal of Medicine, vol. 346:393-403, No. 6, Feb. 7, 2002.

*Urine Analysis for Glucose and Protein,* British Medical Journal, vol. 300, Jun. 2, 1990, John S. Yudkin, et al.

*Identification of Persons at High Risk for Type 2 Diabetes Mellitus: Do We Need the Oral Glucose Tolerance Test?,* Michael P. Stern et al; American College of Physicians-American Society of Internal Medicine, vol. 136, No. 8, pp. 575-581, Apr. 16, 2002.

*Screening for Type 2 Diabetes,* American Diabetes Association, Diabetes Care, vol. 26, Supplement 1, Jan. 2003.

\* cited by examiner

DETERMINATION OF A MEASURE OF A GLYCATION END-PRODUCT OR DISEASE STATE USING TISSUE FLUORESCENCE

CROSS REFERENCES TO CO-PENDING APPLICATIONS

This application claims priority under 35 U.S.C § 120 as a continuation in part of U.S. patent application Ser. No. 10/116,272, entitled "Apparatus And Method For Spectroscopic Analysis Of Tissue To Detect Diabetes In An Individual," filed Apr. 4, 2002, incorporated herein by reference, and claims the benefit of U.S. provisional application 60/515,343, "Determination of a Measure of a Glycation End-Product or Disease State Using Tissue Fluorescence," filed Oct. 28, 2003, incorporated herein by reference; and claims the benefit of U.S. provisional application 60/517,418, "Apparatus And Method For Spectroscopic Analysis Of Tissue To Determine Glycation End-products," filed Nov. 4, 2003, incorporated herein by reference.

FIELD OF THE INVENTION

The present invention generally relates to determination of a tissue state from tissue fluorescence. More specifically, the present invention relates to methods and apparatuses for determining models that relate tissue fluorescence to a tissue state, and for determining fluorescence properties of tissue, and for determination of a tissue state from fluorescence properties and from appropriate models.

BACKGROUND OF THE INVENTION

Diabetes mellitus is a major health problem in the United States and throughout the world's developed and developing nations. In 2002, the American Diabetes Association (ADA) estimated that 18.2 million Americans—fully 6.4% of the citizenry—were afflicted with some form of diabetes. Of these, 90–95% suffered from type 2 diabetes, and 35%, or about 6 million individuals, were undiagnosed. See ADA Report, *Diabetes* Care, 2003. The World Health Organization (WHO) estimates that 175 million people worldwide suffer from diabetes; type 2 diabetes also represents 90% of all diagnoses worldwide. Unfortunately, projections indicate that this grim situation will worsen in the next two decades. The WHO forecasts that the total number of diabetics will double before the year 2025. Similarly, the ADA estimates that by 2020, 8.0% of the U.S. population, some 25 million individuals, will have contracted the disease. Assuming rates of detection remain static, this portends that, in less than twenty years, three of every 100 Americans will be 'silent' diabetics. It is no surprise that many have characterized the worldwide outbreak of diabetes as epidemic.

Diabetes has a significant impact on individual health and the national economy. U.S. health care costs related to diabetes exceeded $132 billion in 2002. Due to the numerous complications that result from chronic hyperglycemia, these costs were distributed over a wide array of health services. For example, between 5 and 10 percent of all U.S. expenditures in the areas of cardiovascular disease, kidney disease, endocrine and metabolic complications, and ophthalmic disorders were attributable to diabetes. See ADA Report, *Diabetes* Care, 2003. These economic and health burdens belie the fact that most diabetes-related complications are preventable. The landmark Diabetes Control and Complications Trial (DCCT) established that a strict regimen of glucose monitoring, exercise, proper diet, and insulin therapy significantly reduced the progression of and risk for developing diabetic complications. See DCCT Research Group, *N Eng J Med,* 1993. Furthermore, the ongoing Diabetes Prevention Program (DPP) has already demonstrated that individuals at risk for diabetes can significantly reduce their chances of contracting the disease by implementing lifestyle changes such a weight loss and increased physical activity. See DPP Research Group, *N Eng J Med,* 2002. ADA has recommended that health care providers begin screening of individuals with one or more disease risk factors, observing: "If the DPP demonstrates a reduction in the incidence of type 2 diabetes as a result of one or more of the [tested] interventions, then more widespread screening . . . may be justified". See ADA Position Statement, *Diabetes Care,* 2003.

The Fasting Plasma Glucose (FPG) test is one of two accepted clinical standards for the diagnosis of or screening for diabetes. See ADA Committee Report, *Diabetes Care,* 2003. The FPG test is a carbohydrate metabolism test that measures plasma glucose levels after a 12–14 hour fast. Fasting stimulates the release of the hormone glucagon, which in turn raises plasma glucose levels. In non-diabetic individuals, the body will produce and process insulin to counteract the rise in glucose levels. In diabetic individuals, plasma glucose levels remain elevated. The ADA recommends that the FPG test be administered in the morning because afternoon tests tend to produce lower readings. In most healthy individuals, FPG levels will fall between 70 and 100 mg/dl. Medications, exercise, and recent illnesses can impact the results of this test, so an appropriate medical history should be taken before it is performed. FPG levels of 126 mg/dl or higher indicate a need for a subsequent retest. If the same levels are reached during the retest, a diagnosis of diabetes mellitus is typically rendered. Results that measure only slightly above the normal range may require further testing, including the Oral Glucose Tolerance Test (OGTT) or a postprandial plasma glucose test, to confirm a diabetes diagnosis. Other conditions which can cause an elevated result include pancreatitis, Cushing's syndrome, liver or kidney disease, eclampsia, and other acute illnesses such as sepsis or myocardial infarction.

Because it is easier to perform and more convenient for patients, the FPG test is strongly recommended by the ADA and is in more widespread use than the other accepted diagnostic standard, the OGTT. The OGTT is the clinical gold standard for diagnosis of diabetes despite various drawbacks. After presenting in a fasting state, the patient is administered an oral dose of glucose solution (75 to 100 grams of dextrose) which typically causes blood glucose levels to rise in the first hour and return to baseline within three hours as the body produces insulin to normalize glucose levels. Blood glucose levels may be measured four to five times over a 3-hour OGTT administration. On average, levels typically peak at 160–180 mg/dl from 30 minutes to 1 hour after administration of the oral glucose dose, and then return to fasting levels of 140 mg/dl or less within two to three hours. Factors such as age, weight, and race can influence results, as can recent illnesses and certain medications. For example, older individuals will have an upper limit increase of 1 mg/dl in glucose tolerance for every year over age 50. Current ADA guidelines dictate a diagnosis of diabetes if the two-hour post-load blood glucose value is greater than 200 mg/dl on two separate OGTTs administered on different days.

In addition to these diagnostic criteria, the ADA also recognizes two 'pre-diabetic' conditions reflecting deviations from euglycemia that, while abnormal, are considered insufficient to merit a diagnosis of diabetes mellitus. An individual is said to have 'Impaired Fasting Glucose' (IFG) when a single FPG test falls between 100 and 126 mg/dl. Similarly, when the OGTT yields 2-hour post-load glucose values between 140 and 200 mg/dl, a diagnosis of 'Impaired Glucose Tolerance' (IGT) is typically rendered. Both of these conditions are considered risk factors for diabetes, and IFG/IGT were used as entrance criteria in the Diabetes Prevention Program. IFG/IGT are also associated with increased risk of cardiovascular disease.

The need for pre-test fasting, invasive blood draws, and repeat testing on multiple days combine to make the OGTT and FPG tests inconvenient for the patient and expensive to administer. In addition, the diagnostic accuracy of these tests leaves significant room for improvement. See, e.g., M. P. Stern, et al., Ann Intern Med, 2002, and J. S. Yudkin et al., BMJ, 1990. Various attempts have been made in the past to avoid the disadvantages of the FPG and OGTT in diabetes screening. For example, risk assessments based on patient history and paper-and-pencil tests have been attempted, but such techniques have typically resulted in lackluster diagnostic accuracy. In addition, the use of glycated hemoglobin (HbA1c) has been suggested for diabetes screening. However, because HbA1c is an indicator of average glycemia over a period of several weeks, its inherent variability combines with the experimental uncertainty associated with currently-available HbA1c assays to make it a rather poor indicator of diabetes. See ADA Committee Report, Diabetes Care, 2003. HbA1c levels of diabetics can overlap those of nondiabetics, making HbA1c problematic as a screening test. A reliable, convenient, and cost-effective means to screen for diabetes mellitus is needed. Also, a reliable, convenient, and cost-effective means for measuring effects of diabetes could help in treating the disease and avoiding complications from the disease.

U.S. Pat. No. 5,582,168 (Samuels) discloses apparatus and methods for measuring characteristics of biological tissues and similar materials. These apparatus and methods are described with respect to measurements of the human eye. In addition, the correction methodologies described by these inventors involve only measurements of the elastically scattered excitation light. Samuels describes a simple linear correction technique. Samuels does not disclose an algorithm or methods by which tissue disease status may be discriminated via noninvasive measurements.

U.S. Pat. No. 6,505,059 (Kollias) discloses instruments and methods for noninvasive tissue glucose level monitoring. Kollias does not describe any method by which measured fluorescence can be corrected for the effects of tissue absorption and scattering. While Kollias indicates that a tissue reflectance measurement can be made to measure tissue scattering directly, it does not indicate how one would use this information to obtain information regarding the tissue fluorescence spectrum. Furthermore, Kollias does not disclose an algorithm or methods by which tissue disease status may be determined from noninvasive measurements.

U.S. Pat. No. 6,571,118 (Utzinger) discloses methods and apparatus for performing fluorescence and spatially resolved reflectance spectroscopy on a sample. While Utzinger describes a technique in which a combination of fluorescence and reflectance measurements are used to characterize biological tissue, the application does not relate to spectroscopy of the skin. Furthermore, the reflectance measurements described in Utzinger are spatially-resolved in nature, that is, the reflectance spectroscopy is to be conducted at one or more specific source-receiver separations. Finally, no algorithm or process is described by which the measured fluorescence may be corrected using the tissue reflectance measurements to obtain or approximate the intrinsic fluorescence spectrum of the tissue in question.

U.S. Patent application 20030013973 (Georgakoudi) discloses a system and methods of fluorescence, reflectance and light scattering spectroscopy for measuring tissue characteristics. Georgakoudi discusses estimation of intrinsic fluorescence using reflectance properties as applied to detection of esophageal cancer and Barrett's esophagus. Georgakoudi does not describe any specific techniques for such estimation.

U.S. Pat. No. 6,088,606 (Ignotz) discloses a system and method for determining the duration of a medical condition. Ignotz mentions fluorescence, but does not use a reflectance spectrum to obtain or estimate an intrinsic fluorescence spectrum. In addition, Ignotz described methods relating to determining the duration of a disease, not for diagnosing or screening for the presence of disease or for quantifying the concentration of specified chemical analytes. Finally, Ignotz does not address skin as a useful measurement site.

U.S. Pat. No. 5,601,079 (Wong) describes an apparatus for the non-invasive quantification of glucose control, aging, and advanced Maillard products by stimulated fluorescence. Wong specifically quantifies Advanced Glycation Endproducts in the blood, not in the skin and/or its structural proteins. In addition, the fluorescence correction methodology involves only measurements of the elastically scattered excitation light. Wong describes only a simple linear correction technique. Finally, Wong does not disclose an algorithm or methods by which tissue disease status may be discriminated via noninvasive measurements.

International patent publication WO 01/22869 (Smits) describes an apparatus for non-invasive determination of skin autofluorescence. The apparatus consists of a broadband uv source (blacklight) that illuminates skin through interchangeable optical bandpass filters. Resulting skin fluorescence is fiber-optically coupled to a compact spectrophotometer. The application proffers AGE concentration in the skin can be inferred from qualitative assessment of skin autofluorescence but it does not describe any means by which the AGE content can be quantified using the device and measurement techniques. The apparatus is intended to assess skin fluorescence in healthy individuals and does not address the utility of the device for disease determination. The application notes that individual skin coloring and substructure can be a measurement interferent but it is silent on techniques or methods to compensate for these variable characteristics.

SUMMARY OF THE INVENTION

The present invention provides a method of determining tissue state in an individual. A portion of the tissue of the individual is illuminated with excitation light, then light emitted by the tissue due to fluorescence of a chemical in the tissue responsive to the excitation light is detected. The detected light can be combined with a model relating fluorescence with disease state to determine a disease state of the individual. The invention can comprise single wavelength excitation light, scanning of excitation light (illuminating the tissue at a plurality of wavelengths), detection at a single wavelength, scanning of detection wavelengths (detecting emitted light at a plurality of wavelengths), and combinations thereof. The invention also can comprise correction techniques that reduce determination errors due to detection of light other than that from fluorescence of a chemical in the tissue. For example, the reflectance of the tissue can lead to errors if appropriate correction is not employed. The invention can also comprise a variety of models relating fluorescence to disease state, including a variety of methods for generating such models. Other biologic information can be used in combination with the fluorescence properties to aid in the determination of tissue state, for example age of the individual, height of the individual, weight of the individual, history of disease in the individual's family, ethnicity, skin melanin content, or a combination thereof. Raman or near-infrared spectroscopic examination can also be used to supply additional information, for example like that discussed in U.S. patent application Ser. No. 10/116,272, entitled "Apparatus And Method For Spectroscopic Analysis Of Tissue To Detect Diabetes In An Individual," filed Apr. 4, 2002. The invention also comprises apparatuses suitable for carrying out the method, including appropriate light sources, tissue sampling devices, detectors, and models (for example, implemented on computers) used to relate detected fluorescence and disease state.

As used herein, "determining a disease state" includes determining the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes. "Diabetes" includes a number of blood glucose regulation conditions, including Type I, Type II, and gestational diabetes, other types of diabetes as recognized by the American Diabetes Association (See ADA Committee Report, Diabetes Care, 2003), hyperglycemia, impaired fasting glucose, impaired glucose tolerance, and pre-diabetes. "Tissue reflectance characteristic" includes any reflectance property of tissue that is useful in correction of detected light, including as examples the tissue reflectance at the fluorescence excitation wavelength, the tissue reflectance at the fluorescence emission wavelength, and the tissue reflectance at other wavelengths found useful for estimating the tissue's intrinsic fluorescence spectrum. A "measure of chemical change due to glycemic control" means any change in the chemical characteristics of tissue that is due to glycemic control, examples including concentration, measurements of the presence, concentration, or change in concentration of glycation end-products in tissue; measurements of the rate or change in the rate of the accumulation of such end-products; measurements of tissue membrane thickness or the change, rate of change, or direction of change of such thickness; tissue properties such as tensile strength, strain, or compressibility, or the change, rate of change, or direction of change of such property. A "measure of glycation end-product" means any measure of the presence, time, extent, or state of tissue associated with hyperglycemia, including, as examples, measurements of the presence, concentration, or change in concentration of glycation end-products in tissue; measurements of the rate or change in the rate of the accumulation of such end-products; measurements of the presence, intensity, or change in intensity of fluorescence at wavelengths known to be associated with tissue glycation end-products; and measurements of the rate or change in the rate of the accumulation of such fluorescence. "Determination of a tissue state" comprises determination of disease state, determination of a measure of chemical change due to glycemic control, determination of a measure of glycation end-products in tissue, or a combination thereof. When light is described as having a "single wavelength", it is understood that the light can actually comprise light at a plurality of wavelengths, but that a significant portion of the energy in the light is transmitted at a single wavelength or at a range of wavelengths near a single wavelength.

BRIEF DESCRIPTION OF THE DRAWINGS

The drawings, which are not necessarily to scale, depict illustrative embodiments and are not intended to limit the scope of the invention.

DETAILED DESCRIPTION OF THE INVENTION

Figure 1:
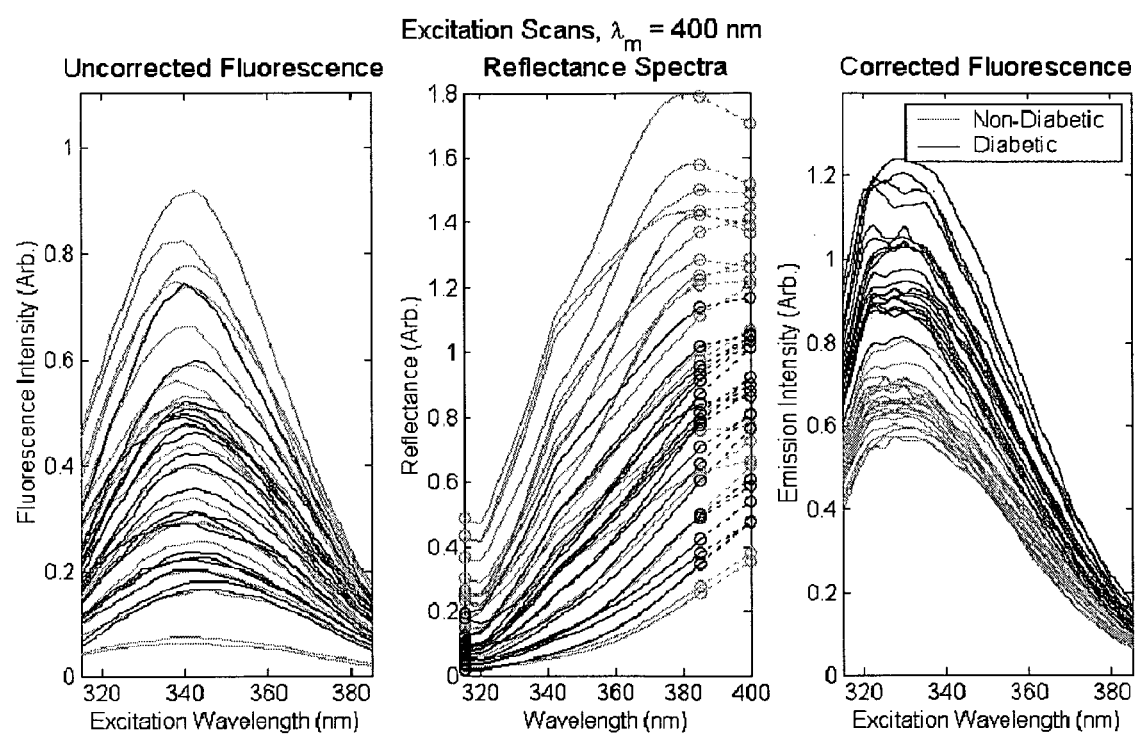
FIG. 1 is a graph of excitation spectra in which the excitation wavelength was scanned from 315 to 385 nm while measuring the emitted fluorescence at a fixed wavelength of 400 nm.

Exposure of proteins to glucose generally leads to non-enzymatic glycation and glycoxidation, a process known as the Maillard reaction. The stable endproducts of the Maillard reaction are collectively denoted Advanced Glycation End-products (AGEs). In the absence of significant clearance, these AGEs accumulate at rates proportional to the average level of glycemia. The Maillard reaction can be viewed as an aging process that occurs routinely in health and at an accelerated rate in diabetics due to the presence of chronic hyperglycemia. In skin, collagen is the most abundant protein and readily undergoes glycation. Skin collagen AGEs commonly take the form of fluorescent crosslinks and adducts; pentosidine (a crosslink) and carboxymethyl-lysine (CML, an adduct) are two well-studied examples of skin-collagen AGEs. Other examples of AGEs include fluorolink, pyrraline, crosslines, $N^\epsilon$...-(2-carboxyethyl) lysine (CEL) glyoxal-lysine dimer (GOLD), methylglyoxal-lysine dimer (MOLD), 3DG-ARG imidazolone, vesperlysines A, B, C, and threosidine. One common measure of aggregate AGE production and concomitant collagen cross-linking is the level of collagen-linked fluorescence (CLF). CLF is typically measured in vitro by monitoring fluorescence emission of chemically isolated collagen in the 400–500 nm region after excitation at or near 370 nm. See Monnier, *NEJM*, 1986.

The relatively long half-life ($t_{1/2} \cong 15$ yr) of skin collagen and the fluorescent properties of many of its associated AGEs make these species potential indicators of cumulative tissue glycemia. CLF intensity and levels of specific skin AGEs are correlated with the presence and severity of end-organ diabetes complications such as joint stiffness, retinopathy, nephropathy, and arterial stiffness. See Buckingham, *Diabetes Care*, 1984; Buckingham *J Clin Invest*, 1990; Monnier, *NEJM* 1986; Monnier, *J Clin Invest* 1986; Sell, *Diabetes*, 1992. In the largest such study to date, the DCCT Skin Collagen Ancillary Study Group evaluated a number of skin collagen variables from punch biopsies that were donated by a large fraction of the study's participants. These researchers found that skin AGEs were significantly correlated with the presence and clinical grade of diabetic neuropathy, nephropathy, and retinopathy. See Monnier et al., *Diabetes*, 1999.

The present invention can determine the diabetic state of a subject using one or more noninvasive fluorescence measurements. The invention can illuminate a portion of the tissue of the individual (e.g., a portion of the skin) with excitation light and detect fluorescent light emitted by the tissue. The fluorescence measurements can include at least one set of excitation and emission wavelengths corresponding to the CLF window described above. The characteristics of the fluorescent light convey information about the disease state of the tissue under interrogation. The invention can apply additional processing algorithms to the measured fluorescence before imposing a simple numerical threshold or a more detailed mathematical model to relate the optical information to disease state. In other embodiments, the output of the thresholding process or mathematical model can be a quantitative measure of diabetes-induced chemical change in the tissue of the individual being measured rendered without regard to the individual's diabetic status. In additional embodiments, the invention can utilize a quantitative measure of diabetes-induced chemical changes in order to further infer or classify the diabetic status of the individual undergoing measurement.

Determining a Fluorescence Property of Tissue

Tissue fluorescence is initiated when tissue is illuminated by light that promotes electrons in various molecular species to excited energy levels. Some of the excited molecules decay radiatively, emitting light as the electrons return to a lower energy state. The remitted fluorescence is always of a longer wavelength (lower photon energy) than that of the excitation. The absorption and fluorescence spectra of biomolecules are typically broad and overlapping. Most tissues will absorb a wide range of wavelengths. For a given excitation wavelength, the remitted fluorescence spectrum is often correspondingly broad. Several factors impact the useful range of excitation and emission wavelengths. The fluorescing species (e.g. pentosidine) typically absorb most strongly in the UVA (315–400 nm) and remit in the UVA through short wavelength visible range (340–500 nm). The long wavelength limit of the excitation and emission range is usually imposed by the electronic structure of the fluorescing components. Optical safety considerations can limit the shortest practical excitation wavelengths to the UVA or longer wavelengths. The threshold limit values for optical exposure decrease dramatically for wavelengths below 315 nm. Consequently, safe exposure times for wavelengths in the UVB (280–315 nm) can be too brief for effective spectral data acquisition.

Only gross biochemical and morphological tissue information can be obtained if the spectral selectivity of either the excitation or emission sections of a fluorimeter is relatively coarse. A more useful approach is to consider the emission at a particular wavelength (or narrow range of wavelengths) in response to excitation by light having a single or narrow range of wavelengths—an excitation/emission pair. In practice, the fluorescence signal at a particular wavelength pair can be monitored, or signals corresponding to a collection of excitation/emission pairs can be acquired. Emission spectra (or emission scans) are created when the source wavelength is fixed and fluorescence signal is acquired over a range of emission wavelengths. Similarly, excitation spectra are acquired by fixing the wavelength of emitted fluorescence that is detected while the source wavelength is varied. An excitation-emission map can be used to represent the fluorescence signal as a topographic surface covering a range of excitation and emission wavelengths. Emission and excitation spectra correspond to orthogonal sections of such a map. The points falling on the diagonal of an excitation-emission map, that is, where the excitation and emission wavelengths are equal, indicate the intensity of elastically scattered photons that are reflected by the tissue back to the detection system. These 'reflectance' measurements can be obtained by synchronous scanning of both the excitation and emission monochromators in a fluorimeter or by a separate dedicated apparatus. Both fluorescence and reflectance measurements can be used to ascertain the true or 'intrinsic' fluorescence properties of an optically turbid medium such a biological tissue.

When excitation light is launched into the tissue, it is subject to scattering and absorption processes that vary with the optical properties of the site under interrogation, the excitation wavelength, and the optical probe geometry. Emitted fluorescent light is also subject to wavelength- and location-dependent absorption and scattering as it propagates through the tissue prior to emergence and collection. Often, the tissue property of interest is its 'intrinsic' fluorescence, defined as the fluorescence emitted by a specimen that is homogeneous, nonscattering, and optically dilute. In order to accurately characterize the intrinsic fluorescence spectrum of the tissue of interest, the spectra-altering effects of scattering and absorption that are impressed upon the excitation and emitted light can be removed. Variations due to subject-to-subject and site-to-site differences can overwhelm the subtle spectral variations indicative of tissue status. Spectral correction based upon the tissue optics of each subject (at the same site as the fluorescence measurement, or at a different site having a predictable relationship to the site) can reveal the intrinsic fluorescence spectra of the molecules of interest. This intrinsic correction mitigates the variations across and within subjects, unmasking the spectral features relating to presence and state of disease.

The data described in this example were collected with a SkinSkan fluorimeter (marketed by Jobin-Yvon, Edison, N.J., USA). The excitation and emission sides of the SkinSkan system have dual scanning ⅛-m grating monochromators, accomplishing a ~5 nm system bandpass. Excitation light is provided by a 100W Xe-arc lamp and is f/number matched to a bifurcated fiber probe containing 31 source and 31 detection fibers. The fibers have 200-micron core diameters and are randomly arranged in a 6-mm diameter circular bundle within a ferrule, the distal end of which serves as the skin interface. The output ends of the detection fibers are stacked into an input ferrule, and the fibers' width forms the entrance slit to the first input monochromator. Optical detection is accomplished with a photomultiplier, the gain of which can be controlled via software. Whenever noninvasive spectroscopy was performed, background measurements of a uniformly reflecting material (2% Spectralon, LabSphere, North Sutton, N.H., USA) were also obtained to facilitate removal of the instrument lineshape. In addition, the SkinSkan system provides a silicon photodetector that independently monitors the excitation lamp, allowing for correction for lamp intensity fluctuations. Thus, 'measured' skin fluorescence values, $F_{meas}$, are reported as:

$$F_{meas}(\lambda_x, \lambda_m) = \frac{F_{tiss}(\lambda_m) - I_{DC}}{L(\lambda_x; t_{tiss})} \cdot \frac{L(\lambda_m; t_{back})}{R_{back}(\lambda_m) - I_{DC}}, \quad \text{Eq 1}$$

where $\lambda_x$ is the excitation wavelength, $\lambda_m$ is the emission wavelength, $F_{tiss}$ is the 'raw' fluorescence at the detector, $I_{DC}$ is the PMT dark current, L is the excitation lamp intensity, t denotes time, back refers to the Spectralon background, and $R_{back}$ is the reflectance of the Spectralon background. Similarly, measured skin reflectance values, $R_{meas}$ are reported as:

$$R_{meas}(\lambda) = \frac{R_{tiss}(\lambda) - I_{DC}}{L(\lambda; t_{tiss})} \cdot \frac{L(\lambda; t_{back})}{R_{back}(\lambda) - I_{DC}} \quad \text{Eq 2}$$

where $R_{tiss}$ is the 'raw' tissue reflectance signal at the detector. When the SkinSkan system is used for both fluorescence and reflectance measurements, it is required that a different PMT bias voltage be used for each measurement modality in order to avoid detector saturation.

Figure 2:
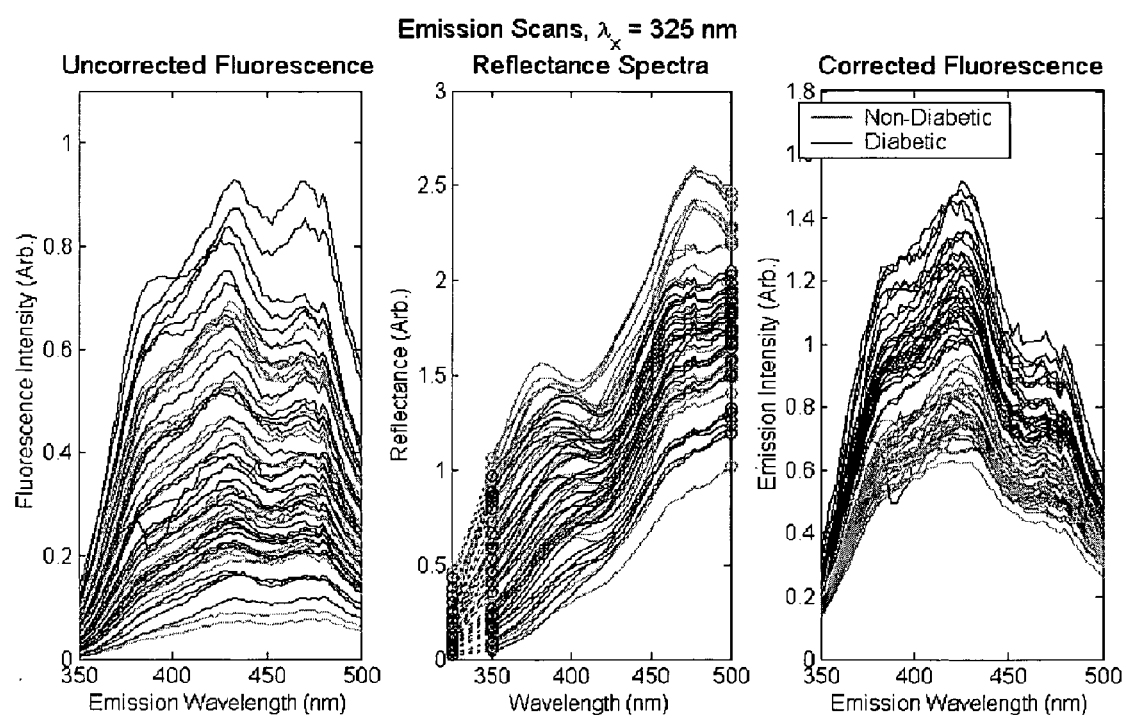
FIG. 2 is a graph of emission scan data in which the excitation was fixed at 325 nm and the fluorescence was monitored by scanning the detection sub-system from 340 to 500 nm.

Typical measured fluorescence spectra of skin are shown in the left panels of FIGS. 1 and 2. These figures illustrate spectra obtained in two different wavelength ranges under different collection modalities. FIG. 1 shows excitation spectra in which the excitation wavelength was scanned from 315 to 385 nm while measuring the emitted fluorescence at a fixed wavelength of 400 nm. FIG. 2 presents emission scan data in which the excitation was fixed at 325 nm and the fluorescence was monitored by scanning the detection sub-system from 340 to 500 nm. All spectra were obtained from the volar forearms of 17 diabetic and 17 non-diabetic subjects between the ages of 40 and 60 years. The center panel of these figures depicts the measured reflectance spectra. Each reflectance spectrum corresponds to a specific fluorescence spectrum and was acquired at same site on the same subject. The fluorescence and reflectance spectra demonstrate typical variations resulting from imperfect probe repositioning, environmental changes and subject-to-subject physiological differences. These variations can exceed the spectral variations due to disease state and hamper the diagnostic utility of the measured spectra. In order to accurately discriminate or quantify disease state, additional tissue-specific spectral corrections can be applied to obtain the intrinsic tissue fluorescence. One approximation for estimating the intrinsic fluorescence spectrum, $F_{corr}$, involves dividing the measured fluorescence spectrum by the product of the roots of the measured reflectance at the excitation and/or emission wavelengths (see, for example, Finlay et al., *Photochem Photobiol*, 2001, and Wu et al., *Appl Opt*, 1993):

$$F_{corr}(\lambda_x, \lambda_m) = \frac{F_{meas}(\lambda_x, \lambda_m)}{R_{meas}(\lambda_x)^k R_{meas}(\lambda_x)^n}; n, k < 1 \quad \text{Eq 3}$$

The optimum values for n and k are dependent on the arrangement of source and detector fibers, and can be determined empirically. Intrinsic fluorescence spectra obtained from the spectra of FIG. 1–2 using the correction function of Equation 3 with values of k=0.5 and n=0.7, are shown in the right panels of these figures. Note that the intrinsic correction has removed much of the inter-patient variation, and coarse groups of spectra corresponding to disease state can now be visually resolved.

The values of n and k used in the intrinsic corrections illustrated in FIGS. 1 and 2 were selected in order to minimize the spectroscopic variation associated with repeated insertions of a study participant's forearm into the measurement device. If multiple spectra are collected from each participant on a patient visit, then the spectroscopic insertion variation, $S_{insert}$, of the ith spectrum for subject j can be expressed as the absolute deviation of that spectrum from the subject's median:

$$S_{insert_{i,j}}(\lambda,n,k)=abs[F_{corr_{i,j}}(\lambda,n,k)-\text{median}(F_{corr_{\cdot,j}}(\lambda,n,k))]/\text{median}(F_{corr_{\cdot,j}}(\lambda,n,k)). \quad \text{Eq 4}$$

An aggregate measure of insertion variation is then the variance of $S_{insert}$:

$$v_{insert}(\lambda,n,k)=\text{var}(S_{insert}(\lambda,n,k)). \quad \text{Eq 5}$$

Figure 3:
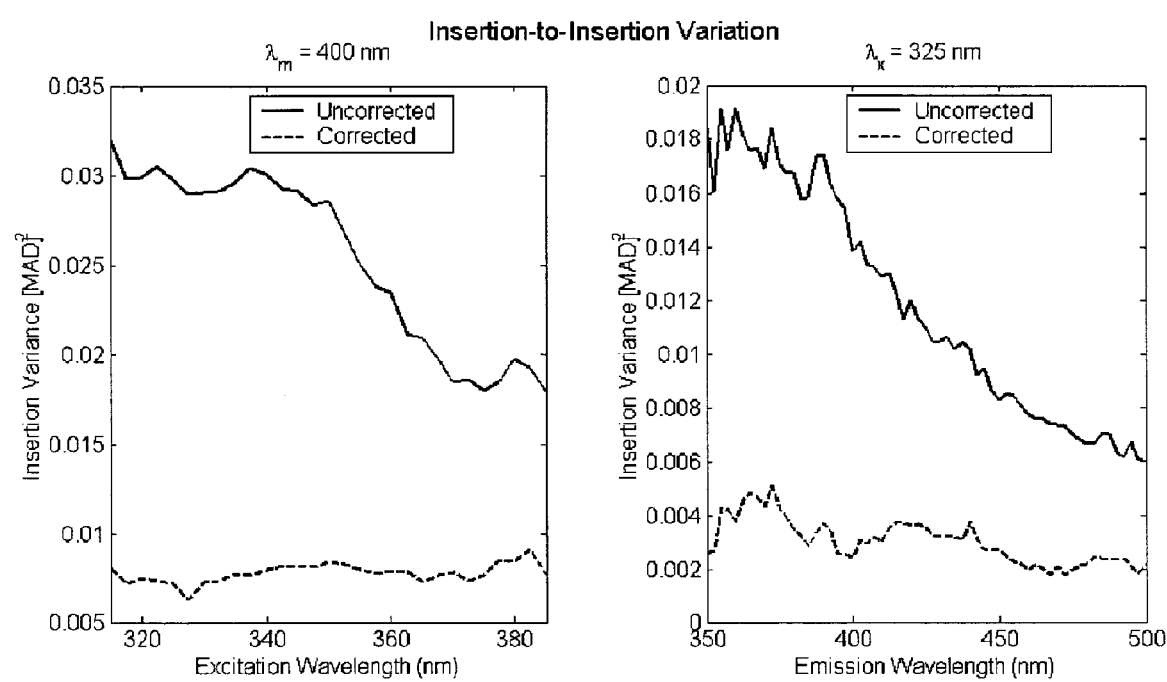
FIG. 3 is a depiction of the insertion variance of the measured (solid lines, 'uncorrected') and intrinsic-corrected spectra (dashed lines, k=0.5, n=0.7) spectra in FIGS. 1 and 2.

FIG. 3 depicts the insertion variance of the measured (solid lines, 'uncorrected') and intrinsic-corrected spectra (dashed lines, k=0.5, n=0.7) spectra in FIGS. 1 and 2. It can be seen that the intrinsic correction process reduces the insertion variance by approximately a factor of four over the full wavelength range. Under the presumption that the intrinsic fluorescence of the tissue does not change from insertion to insertion, this procedure mitigates a portion of the corrupting effects of variation in tissue optical properties.

A variety of other procedures can accomplish intrinsic fluorescence correction. For example, a number of methods have been described by which the measured fluorescence can be corrected using knowledge of the measured reflectance, tissue optical properties, and probe-dependent parameters. See, e.g., Gardner et al., *Appl Opt,* 1996, Zhang et al., *Opt Left,* 2000; Muller et al., *Appl Opt,* 2001. In addition, intrinsic fluorescence corrections can be made using a procedure in which the correction parameters for a given fluorescence probe are created by measuring one or more tissue phantoms for which the fluorescence, absorption, and scattering properties have been well-characterized. This procedure can also be accomplished via Monte-Carlo or other computer simulation of the optical probe's response to media with known optical properties. Any of these processes can be used to correct for the effects of tissue optical properties in noninvasive skin fluorescence measurements. A multi-channel optical probe as described here can enable the measurement of optical properties of the tissue. The optical properties can be determined by solving analytic expressions given multi-channel fluorescence and/or reflectance measurements. Alternatively, optical properties can be estimated from the spectroscopic measurements by comparison with look-up tables relating measured values to predetermined optical property values. Such look-up tables can be generated from numerical models that simulate multi-channel intensity measurements over a range of simulated optical properties. Look-up tables can also be constructed from experimental measurements of tissue-like phantoms spanning a range of optical properties. The measured or estimated optical properties can then be applied to correct for the spectral distortion they induce on incident and fluorescent light. Correction can be accomplished by comparison to a probe calibration tables that can be derived either numerically or experimentally. Inversion algorithms of fluorescence spectroscopy can also be applied to extract the intrinsic dermal fluorescence once measured or estimated optical properties of the tissue have been determined. Alternative methods for multi-channel optical correction of tissue fluorescence include soft-model techniques such as described above (Eq 3). A multi-channel measurement can be used to mitigate the impact of epidermal pigmentation and superficial blood content. For example, by taking the ratio of the reflectance measurement at adjacent channels (Eq 6), the filtering effects of the epidermis are essentially removed, yielding a ratio of transfer functions of the two channels and thus the tissue layers that they interrogate.

$$R_1 = I_0 \exp(-\mu_{a,epi} \cdot 2t_{epi}) T_1(\mu_{a,derm}, \mu_{s,derm}),$$

$$R_2 = I_0 \exp(-\mu_{a,epi} \cdot 2t_{epi}) T_2(\mu_{a,derm}, \mu_{s,derm}),$$

$$R_{norm} = R_1/R_2 = T_1/T_2, \quad \text{Eq 6}$$

Applying techniques per Equation 6, to the respective channels' fluorescence signals yields a fluorescence transfer function that can provide useful fluorescence information with the masking effects of the epidermis and upper dermis largely eliminated. Spectroscopic data from individual channels can be fused and/or combined to provide multivariate techniques additional spectral information that may yield more accurate and/or robust quantification and classification models.

While the examples described here generally concern steady-state fluorescence measurements without regard to polarization, it is possible to apply these methods to other fluorescence measurement modalities. For example, frequency-domain fluorescence spectroscopy, in which the excitation light is amplitude-modulated at RF frequencies and the phase and modulation of the emission light are monitored, can be suitable. Another suitable approach involves time-resolved techniques, in which a short burst of excitation light is applied to the tissue, after which the time-evolution of the resulting fluorescence emission is sampled. Both frequency-domain and time-resolved measurements add the capability to monitor, for example, fluorescence lifetime, a parameter that can provide additional discrimination power. In addition, using polarized excitation light and polarization-sensitive detection, it is possible to measure the fluorescence anisotropy, defined by $r=(I_\parallel - I_\perp)/(I_\parallel + 2 I_\perp)$, where $I_\parallel$ and $I_\perp$ are the fluorescence intensities with polarization parallel and perpendicular to that of a linearly polarized excitation beam. Fluorescence anisotropy measurements can separate signals from fluorophores with overlapping spectra but different rotational correlation times or molecular orientations. In addition, any of these techniques can be used in conjunction with an imaging methodology such as microscopy or macroscopic scanning of the excitation beam in order to acquire information about the spatial distribution of fluorophores. Any of the above-mentioned methods can be used in conjunction with a measurement technique that allows depth discrimination, such as a confocal detection system or optical coherence tomography, to add information concerning the distribution of fluorophores with respect to depth beneath the tissue surface.

Determining a Model Relating Fluorescence Properties to Disease State or Chemical Changes The relationship between tissue fluorescence properties at one or more wavelengths and diabetes disease state is typically not apparent upon visual inspection of the spectral data. Because this is the case, it is usually necessary that a multivariate mathematical relationship, or 'model', be constructed to classify tissue disease states or to quantify chemical changes using intrinsic fluorescence spectra. The construction of such a model generally occurs in two phases: (i) collection of 'calibration' or 'training' data, and (ii) establishing a mathematical relationship between the training data and the disease states or reference concentrations represented in the training data.

During the collection of training data, it can be desirable to collect fluorescence data from many individuals, representing all disease states or reference values one wishes to characterize with the model to be constructed. For example, if one wishes to construct a model that separates diabetics from nondiabetics, it can be desirable to collect representative spectra from a wide variety of both types of individuals. It can be important to collect these data in a manner that minimizes the correlation between disease state and other parameters that can result in fluorescence variation. For example, the natural formation of collagen AGEs in health results in a correlation between skin AGE content and chronological age. It can be important, therefore, to obtain spectra from diabetics and nondiabetics spanning the ages for which the classification model is desired to be applicable. Alternatively, if one wished to construct a model that quantified the level of a specific skin collagen AGE, it can be advisable to collect spectroscopic data spanning a wide range of AGE reference values each day rather than to measure all individuals having the smallest AGE concentrations early in the study and all individuals with larger AGE concentrations later in the study. In the latter case, a spurious correlation arises between AGE concentration and time, and if there are instrumental trends over the course of the study, the resulting model might be calibrated to instrument state rather than analyte concentration.

As the training data are collected, additional reference information can be collected in order to later construct an appropriate classification model. For example, if the classification model is to predict diabetic state, the diabetes status of some or all of the individuals represented in the training set can be collected and associated with the corresponding spectroscopic training data. Alternatively, the classification model can predict the level of a certain chemical species in the skin, such as glycated collagen, glycated elastin, a specific AGE such as pentosidine or CML, or other proteins modified by the hyperglycemic conditions associated with diabetes mellitus. In these cases, skin biopsy specimens can be collected from individuals during the collection of training data. In addition, if other ancillary information, such as age, body mass index, blood pressure, HbA1c, etc. is to be used in generating later disease state assessments, this information can be collected for some or all spectra in the training set.

After the training data are collected, a multivariate model can be constructed to relate the disease states associated with the training data to the corresponding spectroscopic information. The exact model can be chosen based upon the ultimate goal of the training phase. There are at least two types of multivariate models that one might construct. In the first, the goal of the training process is to create a model that correctly classifies the disease state of the measured tissue. In this case, the output of the model is an assignment to one or more discrete classes or groups. These classes or groups might represent different grades or manifestations of a particular disease. They might also represent various degrees of risk for contracting a particular disease or other subgroups of the population that are pertinent to the disease state in question. For the second model type, the goal is to provide a quantitative estimate of some diabetes-induced chemical change in the system. The output of this model is continuously variable across the relevant range of variation and is not necessarily indicative of disease status.

Classification of Tissue Disease Status

Figure 4:
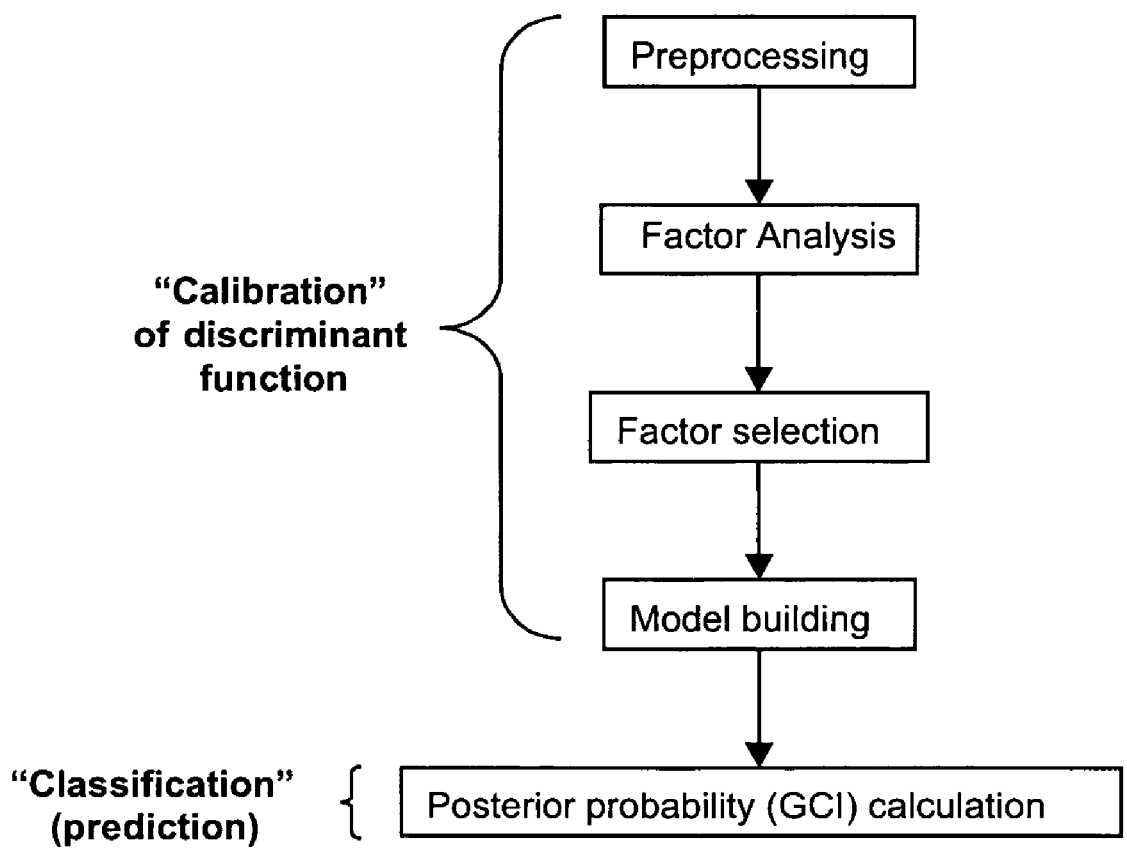
FIG. 4 is a diagrammatic representation of model-building steps typically followed when the end goal is to use the model to assess tissue disease state.

The model-building steps typically followed when the end goal is to use the model to assess tissue disease state are depicted diagrammatically in FIG. 4. The first step, spectral preprocessing, involves pre-treatment, if any, of the spectral data including, for example, background-correction and intrinsic-fluorescence correction steps as described above. In the second step, the dimensionality of the data set can be reduced by employing a factor analysis method. Factor analysis methods allow an individual spectrum to be described by its scores on a set of factors rather than the spectral intensities at each collected wavelength. A variety of techniques can be utilized in this step; Principal Components Analysis (PCA) is one suitable method. The factors generated, for example, by Partial Least-Squares (PLS) regression onto a reference variable associated with disease status can also be used. After the factors have been generated, those factors that are most useful for classification can be selected. Valuable factors typically exhibit a large separation between the classes while having low within-class variance. Factors can be chosen according to a separability index; one possible method for calculating the separability index for factor f is:

$$Separability_f = \frac{|\bar{x}_{1,f} - \bar{x}_{2,f}|}{s_{1,f}^2 + s_{2,f}^2}, \quad \text{Eq 6}$$

where $\bar{x}_{1,f}$ is the mean score for class 1, $\bar{x}_{2,f}$ is the mean score for class 2, and $s^2$ represents variance of the scores within a class.

Figure 5:
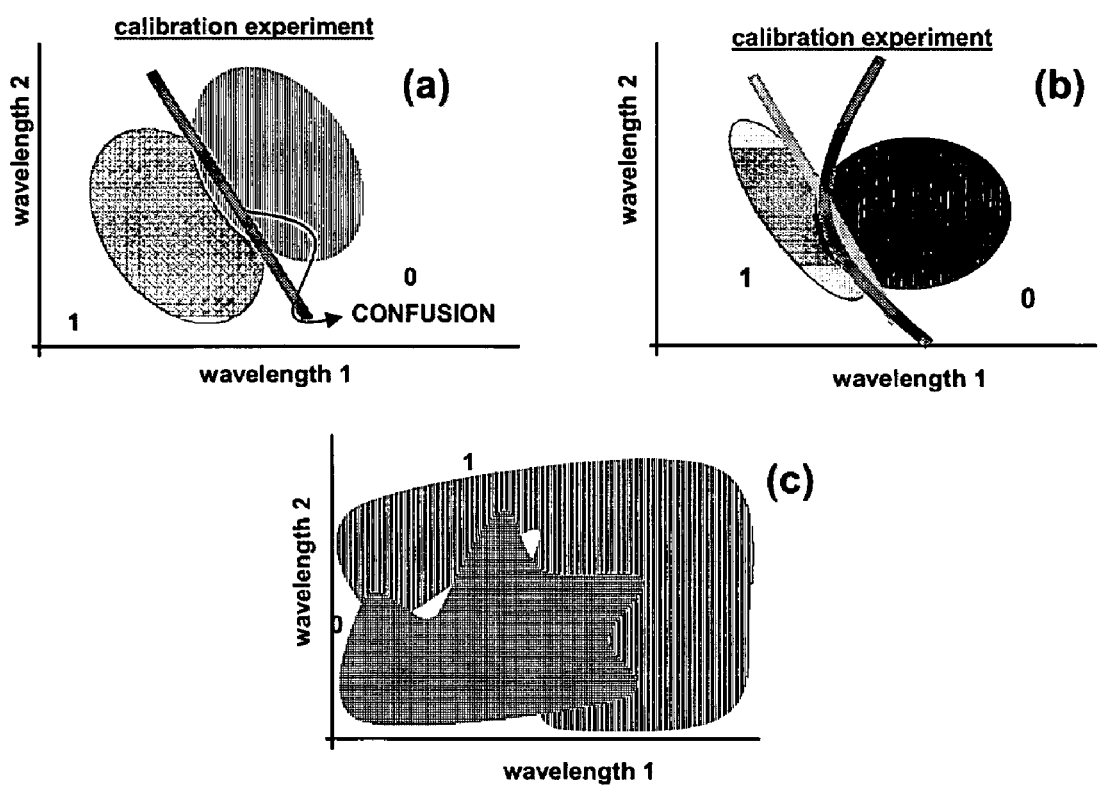
FIG. 5 is an illustration of the manner in which a discriminant function might find the best separation between two groups.
Figure 6:
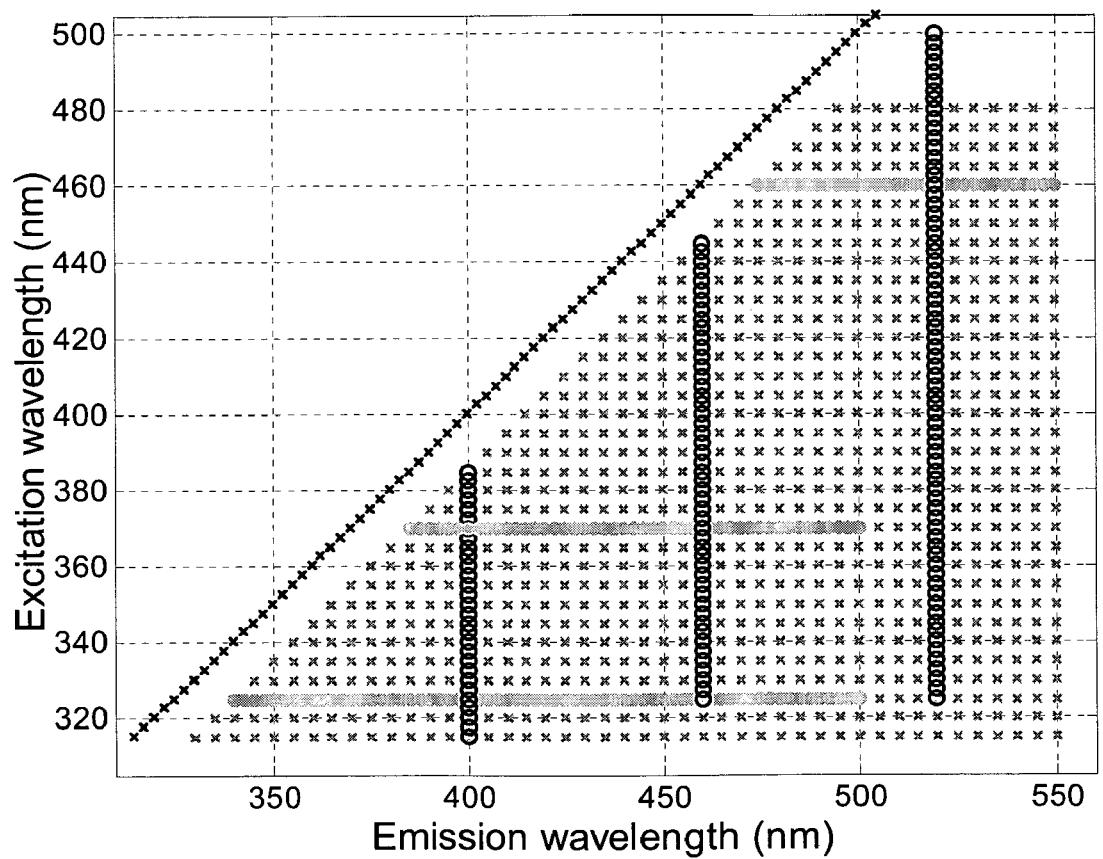
FIG. 6 is an illustration of data sets and their corresponding wavelength regions.

Finally, a technique for separating the data into the various classes can be selected. A variety of algorithms can be suitable, and the optimum algorithm can be selected according to the structure of the training data. In Linear Discriminant Analysis (LDA), a single linear function that best separates the multidimensional spectroscopic data into the reference classes observed in the training period is constructed. In Quadratic Discriminants Analysis, a quadratic discriminant function is constructed. FIG. 5 illustrates the manner in which the discriminant function might find the best separation between two groups—it depends on the structure of the data. In some cases (FIG. 5(a)), a linear discriminant function is sufficient to separate the classes. As the multi-dimensional structure of the classes becomes more complex, however, more sophisticated classifiers, such as quadratic functions, are required (FIG. 5(b)). In some situations (FIG. 5(c)), the structure of the data makes even quadratic discriminant analysis difficult and other classification methods are more appropriate.

A number of suitable classification algorithms exist. For example, k-nearest neighbors, logistic regression, hierarchical clustering algorithms such as Classification and Regression Trees (CART), and machine learning techniques such as neural networks, can all be appropriate and useful techniques. A detailed discussion of such techniques is available in Huberty, *Applied Discriminant Anaylsis*, Wiley & Sons, 1994 and Duda, Hart, and Stork, *Pattern Classification*, Wiley & Sons, 2001.

Quantitation of Diabetes-Induced Chemical Modifications

If the end goal is to quantify the concentration of an analyte or a class of analytes that are embedded in the tissue, a different approach can be taken in the model-building process. In this case, a set of (typically continuous) reference values for the analyte(s) in question can be obtained for some or all spectra in the training set. For example, in the event that the model is to quantify the level of pentosidine in skin collagen, the reference concentrations associated with each spectrum in the training set can come from pentosidine assays conducted on skin punch biopsy specimens obtained during calibration. In the event that the biopsy process is too invasive for the study participants, some surrogate for AGE-related chemical changes can also be used. For example, under the assumption that FPG values increase as the degree of diabetes progression increases, a reasonable compromise can collect FPG data as a surrogate for skin AGE concentration. HbA1c and OGTT information can be used similarly.

Calibration models used to predict quantitative values associated with a test set can be constructed by forming a mathematical relation between reference values and associated spectral data. A variety of algorithms are suitable. For example, in Principal Components Regression (PCR) the calibration data are first decomposed into a set of orthogonal scores and loadings, and then the reference values are regressed onto the scores of the first N PCA factors. Another suitable method is Partial Least-Squares (PLS) regression, in which a set of factors are constructed so that the squared covariance between the reference values and the scores on each successive PLS loading vector is maximized. These procedures and others have been summarized by Martens and Naes in Multivariate Calibration, Wiley & Sons (1989).

Quantitative calibration models are certainly not limited to the regression techniques described here. Those skilled in the art will recognize that a variety of other approaches is available, including other regression techniques, neural networks, and other nonlinear techniques.

Determining Disease State or Chemical Changes from a Fluorescence Property

After model construction, fluorescence measurements can be made on new specimens having an unknown disease state or diabetes-related chemical change. The method by which the disease state or chemical properties of the new specimen are determined can be dependent of the type of model constructed in the training phase.

Classification of Tissue Disease Status

As mentioned above, a variety of models is available for discrimination of various diabetic states from measured fluorescence properties. For example, when the method of Quadratic Discriminants Analysis is used, the new fluorescence spectrum is projected onto the factors created with the training data during construction of the classification model, creating a new vector of scores, $x_i$, for the test spectrum. The means $\bar{x}_j$ and covariance matrices $S_j$ of the scores of the training set over the previously-selected factors are computed for each class j. For example, j=1,2 for a two-class (i.e., diabetic vs. non-diabetic) problem. The Mahalanobis distance, $D_{i,j}$, from sample i to class j, then is computed for each vector of scores ($x_i$) by $$D_{i,j} = (x_i - \bar{x}_j)^T S_j^{-1} (x_i - \bar{x}_j).$$   Eq 7

The posterior probability that test sample i is a member of class j, $p(i \in j)$, can be calculated using Equation 8. As with all probabilities, this number ranges between 0 and 1; probabilities close to 1 indicate that an observation lies close to the diabetic class, and probabilities close to 0 indicate that an observation lies close to the non-diabetic class. The probability that sample i is a member of class j is given by $$p(i \in j) = \frac{\pi_{ij} e^{-D_{ij}/2}}{\sum_j \pi_{ij} e^{-D_{ij}/2}},$$   Eq 8 where $\pi_{ij}$ are the prior probabilities that test sample i is a member of class j based on other knowledge (risk factors, etc.). The prior probabilities are parameters that can be tuned in the prediction phase depending, in part, on the diagnostic application of the classification algorithm.

Finally, a threshold can be applied that assigns the new fluorescence measurement to a particular tissue disease state. For example, it might be determined that all fluorescence measurements yielding a posterior probability of diabetes greater than 0.75 will be assigned to the diabetic class. Like the prior probabilities, the exact threshold applied in validation can depend on a variety of factors, including the application, disease prevalence, and socioeconomic ramifications of positive and negative test results.

Quantitation of Diabetes-Induced Chemical Modifications

The output of a quantitative calibration model can be a regression vector that converts the corrected fluorescence spectrum into a quantitative analyte prediction via an inner product:

$$\hat{a} = F_{corr} \cdot b,$$   Eq 9 where $\hat{a}$ is the analyte prediction and b is the regression vector.

The method for generating a quantitative output can vary with the model constructed in the training phase. Final analyte quantitation with, for example, a neural network proceeds by a different process but yields a similar output.

After the construction of either type (i.e., a quantitative model for chemical change or a classification model for tissue disease state) of multivariate model, the accuracy of the model can be tested by predicting the disease status associated with well-characterized 'validation' spectra. A variety of techniques also exist for accomplishing this task. In leave-one-out cross-validation, a single spectrum or set of spectra from the training set are omitted from the model-building process, and then the resulting model is used to predict the disease status associated with the spectra left out of the model. By repeating this process a sufficient number of times, it is possible to develop a mathematical estimate of the performance of the model under new conditions. A more rigorous test of the newly-constructed model is to apply the model to an entirely new data set, or a 'test' set. In this case, the disease status associated with each spectrum is known, but the 'test' spectra are collected at a different time (e.g., subsequent to model-building) than the training data. By comparing the predictions on the 'test' data to the reference values associated with these data, the diagnostic accuracy of the model in question can be assessed independent of the training data.

Example Embodiments

FIGS. 6–10 depict the results of a large calibration study conducted over a period of 3 months. In these experiments, a commercially-available fluorimeter (SkinSkan, Jobin-Yvon, Edison, N.J., USA) was used to acquire noninvasive fluorescence and reflectance spectra from the skin of the volar forearm in study participants. In the training phase, 57 Type 2 diabetic and 148 nondiabetic subjects were measured by fluorescence spectroscopy. Study participants were selected on the basis of their age and self-reported diabetes status. In addition to the subjects' own report of their disease status, FPG and OGTT reference information were also collected for all diabetics and a fraction of the nondiabetics in the study. For these individuals, FPG and 2-hour OGTT values were collected on each of two different days. Spectroscopic measurements were collected on a third day, and no specific fasting requirements or other pre-test preparations were imposed on the study participants.

In this study, several fluorescence data sets were acquired. Three different sets of emission scans were collected at 2.5-nm data spacing: (1) $\lambda_x$=325 nm, $\lambda_m$=340–500 nm, (2) $\lambda_x$=370 nm, $\lambda_m$=385–500 nm, and (3) $\lambda_x$=460 nm, $\lambda_m$=475–550 nm. In addition, three different sets of excitation scans (2.5 nm data spacing) were also collected: (1) $\lambda_m$=460 nm, $\lambda_x$=325–445 nm, (2) $\lambda_m$=520 nm, $\lambda_x$=325–500 nm, and (3) $\lambda_m$=345 nm, $\lambda_x$=315–330 nm. A lower-resolution (10-nm data spacing) excitation-emission map (EEM) was also collected, along with skin reflectance data spanning the range of excitation and emission wavelengths used in the fluorescence data acquisition. These data sets and their corresponding wavelength regions are depicted graphically in FIG. 6, in which the black open circles denote excitation scans, the gray filled circles denote emission scans, the gray x symbols denote the EEM, and the black x symbols denote reflectance scans. Two replicates of each of these data sets were acquired for each study participant. Each replicate spectroscopic dataset was obtained from a different physical region of the volar forearm.

Two different multivariate models were constructed with these training data. The first model classifies new measurements according to their apparent diabetic status. The second model quantifies diabetes-induced chemical changes using the FPG reference values as a surrogate for skin-collagen AGE content.

Classification of Tissue Disease Status

Figure 7:
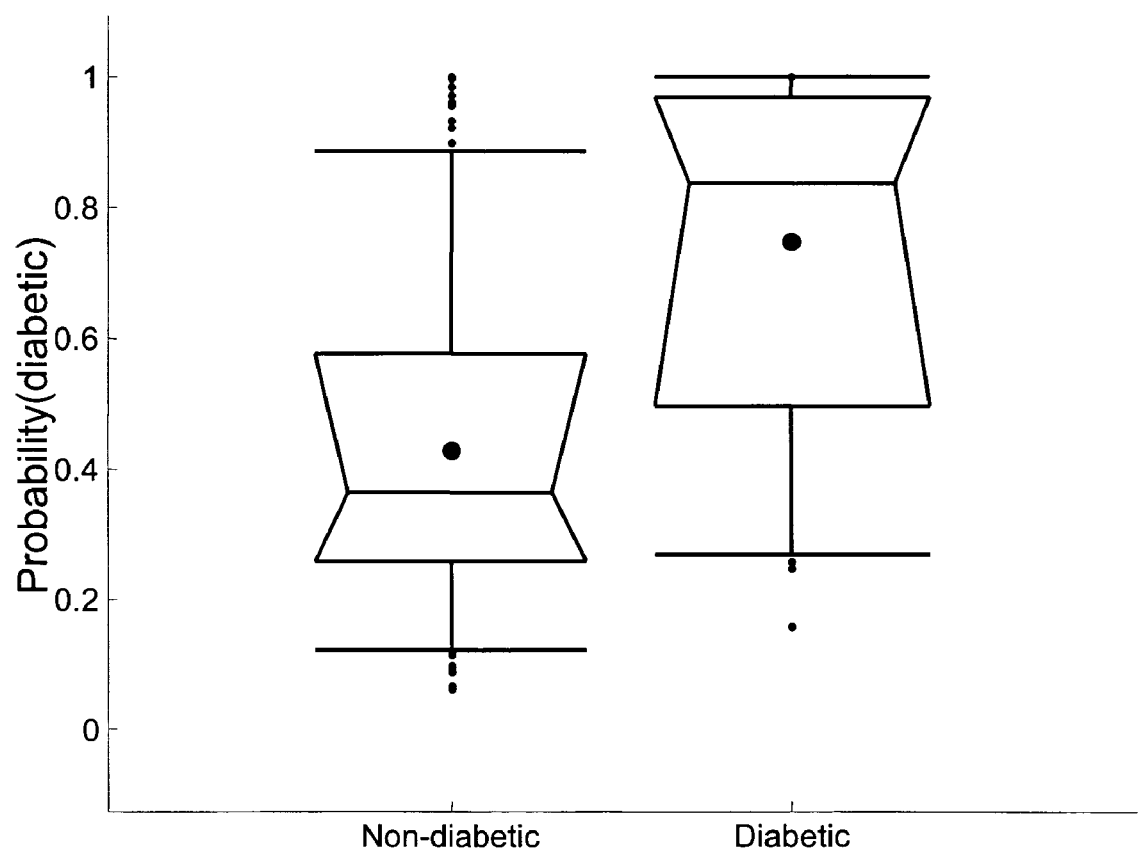
FIG. 7 is a box-and-whisker plot of cross-validate posterior probabilities of membership in the diabetic class for all study participants.

After the completion of the training data collection, all of the noninvasive measurements were pooled along with the reference information (self-reported diabetes status, FPG and OGTT reference values). Post-processing, including intrinsic fluorescence correction using the method described in Eq. 3 with k=0.5 and n=0.7, was first performed on all fluorescence data. The results presented here were obtained by combining the three excitation scans described above into a single large fluorescence spectrum. The PCA factor analysis method was used to reduce the dimensionality of this data set, and QDA was used to construct a classifier using the scores on 5 of the first 25 principal components using the separability index indicated in Equation 6 to identify those PCA factors most useful for class discrimination. The diagnostic accuracy of the QDA classifier was assessed using the method of leave-one-out cross-validation. In this instance, all of the spectroscopic data for a single patient is held out from the training data, an independent QDA model is constructed, and the posterior probability of each spectrum's membership in the diabetic class is computed. FIG. 7 is a box-and-whisker plot of cross-validate posterior probabilities of membership in the diabetic class for all study participants. It can be seen that the known diabetic individuals, in general, exhibit higher probabilities for diabetes than the nondiabetics. As is often the case with diagnostic tests, no single test threshold perfectly separates all diabetics from all nondiabetics with the example data.

One way of summarizing the diagnostic accuracy of the QDA classifier is to plot the True Positive Fraction (i.e., the sensitivity) vs. False Positive Fraction (i.e., 1-specificity) for a range of test thresholds. The area under the resulting Receiver-Operator Characteristic (ROC) curve approaches unity for a perfect classification test and approaches 0.5 for tests that are no better than random chance. The ROC curve from the QDA cross-validation procedure described above is shown as the solid line in FIG. 8. The area under this ROC curve is 0.82, and at the knee of the curve, a sensitivity of approximately 70% is achieved when the false positive rate is approximately 20%. The associated equal error rate, the point at which the sensitivity and false positive rate are equal, is approximately 25%. All of these ROC parameters compare favorably with comparable values from the FPG ROC curve, which is shown as a dashed line for comparison. The ROC curve for the FPG test was computed from a database of over 16,000 individuals participating in the Third National Health and Nutrition Examination Survey, conducted from 1988–1994. The curve was generated by applying various test thresholds to the FPG test values using the study participants' self-declared diabetic status as truth.

Quantitation of Diabetes-Induced Chemical Modifications

Rather than using fluorescence measurements to directly assign a diabetes disease status to an unknown specimen, it can be valuable to generate a quantitative measure of chemical changes that is related to the presence or progression of diabetes. For example, skin biopsies can be assayed for the concentration of pentosidine, CML, or another skin collagen AGE. Those reference values can be used in the construction of a multivariate model as described above. In the current example, such reference data were not available, and the FPG values collected during the training phase were used as surrogates for this chemical information.

A quantitative PLS calibration model was constructed from the same corrected fluorescence data described above. The results presented here were obtained by combining the three excitation scans described above into a single large fluorescence spectrum. A total of three latent variables, or PLS factors, were constructed from the noninvasive fluorescence data and used to model the variation in the FPG reference values. Because most of the fluorescence wavelengths are centered around the CLF window, the spectroscopic changes are presumed to originate, at least in part, with collagen crosslinking and associated diabetes progression. As a result, it is not expected that the FPG test values will serve as perfect surrogates for disease progression.

Figure 9:
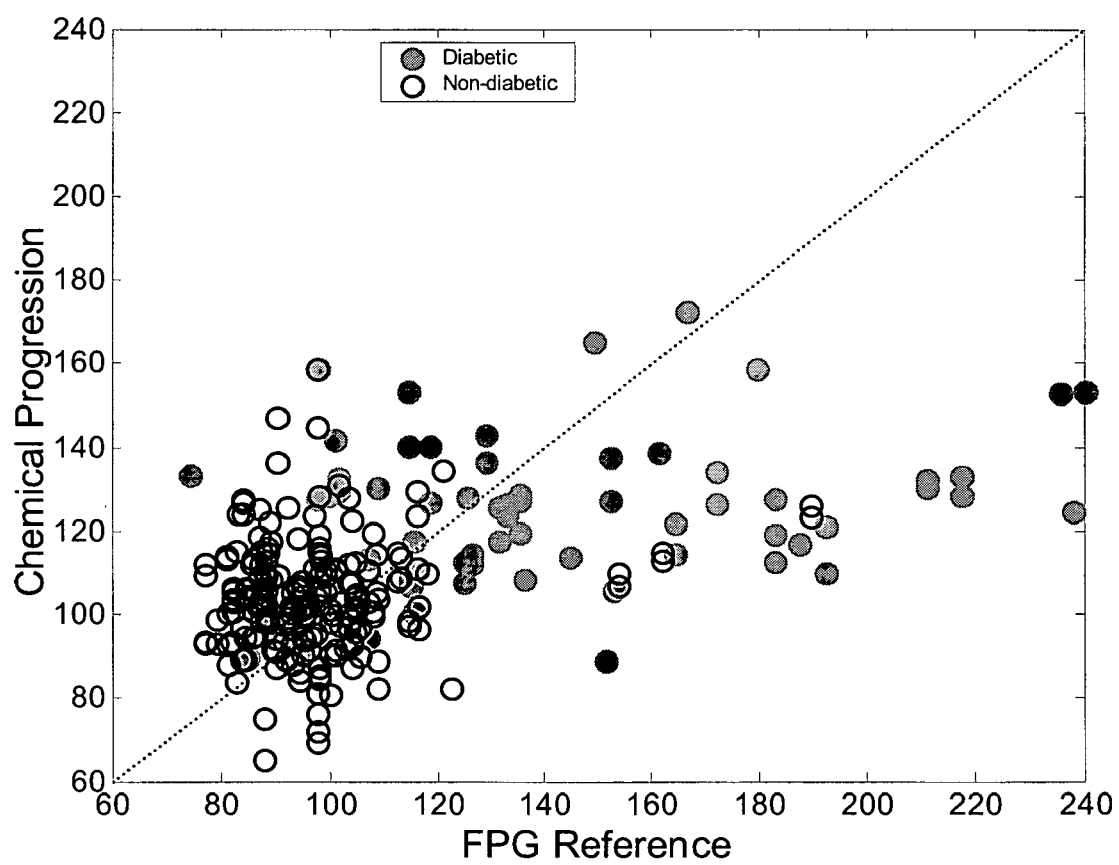
FIG. 9 is an illustration of results of a cross-validation in which all data from a single study participant were rotated out in each iteration.

Results of a cross-validation in which all data from a single study participant were rotated out in each iteration are presented in FIG. 9. The PLS estimates at three model factors are depicted on the y-axis; because the fluorescence changes are presumed to originate with AGE chemistry, this axis is labeled 'Chemical Progression', and the dimensions are left arbitrary. The corresponding FPG value is indicated on the abscissa. Values from diabetic subjects are depicted as solid gray circles, while non-diabetics are represented by open circles. It can be seen that, in general, larger reference values correspond to larger PLS estimates of Chemical Progression, although, as one might expect, the relationship is not perfectly linear. In addition, it can be seen that diabetic individuals exhibit, on average, larger Chemical Progression estimates than do nondiabetic individuals. A reference value more closely aligned with true disease progression, such as one more or skin-collagen AGEs, could produce a model with a more linear relationship.

Figure 8:
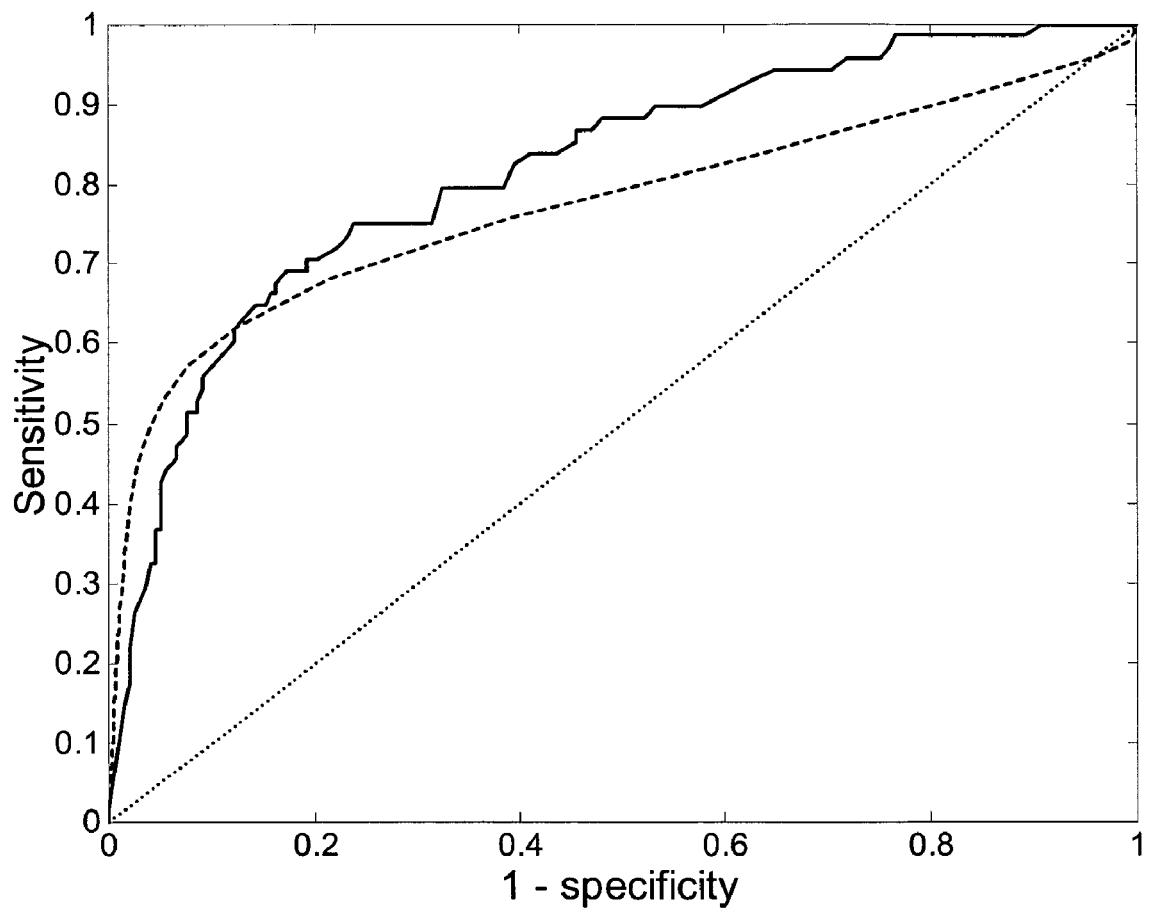
FIG. 8 is an illustration of a receiver-operator curve associated with the present invention and a receiver-operator curve associated with the Fasting Plasma Glucose test.
Figure 10:
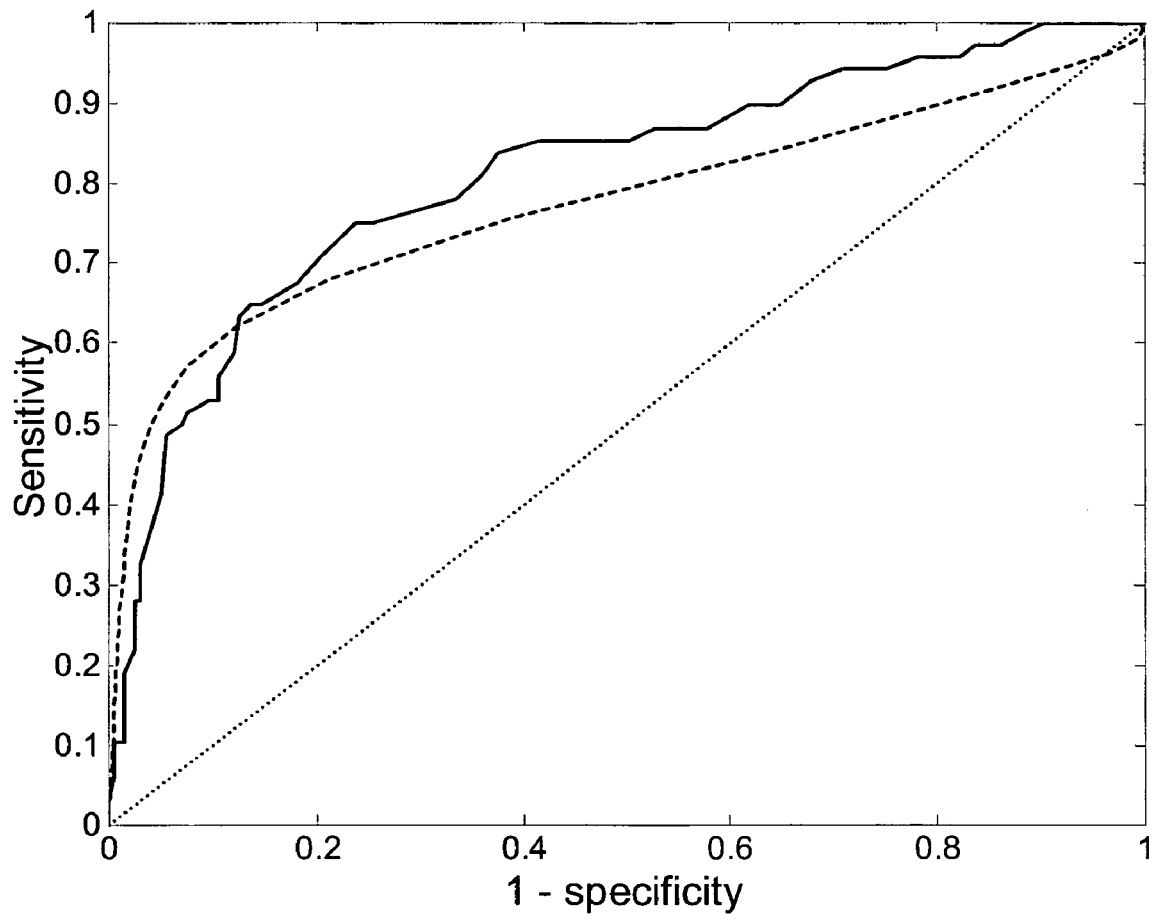
FIG. 10 is an illustration of a receiver-operator curve associated with the present invention and a receiver-operator curve associated with the Fasting Plasma Glucose test.

Although a quantitative model for diabetes-related chemical changes might report only a test value (i.e., without rendering a classification regarding the tissue's disease status), it is also possible to use the output of such a model for classification purposes. One example of such a procedure is illustrated in FIG. 10, which is a ROC curve created from the PLS Chemical Progression estimates depicted in FIG. 9 using the study participants' self-reported diabetic status as truth. The FPG ROC curve from FIG. 8 is reproduced in FIG. 10 for comparison. The area under this ROC curve is 0.81, and at the knee of the curve, a sensitivity of 65% is achieved at a 20% false positive rate. The associated equal error rate, the point at which the sensitivity and false positive rate are equal, is approximately 25%. All of these ROC parameters again compare favorably with comparable values from the FPG ROC curve.

Example Apparatus

Figure 11:
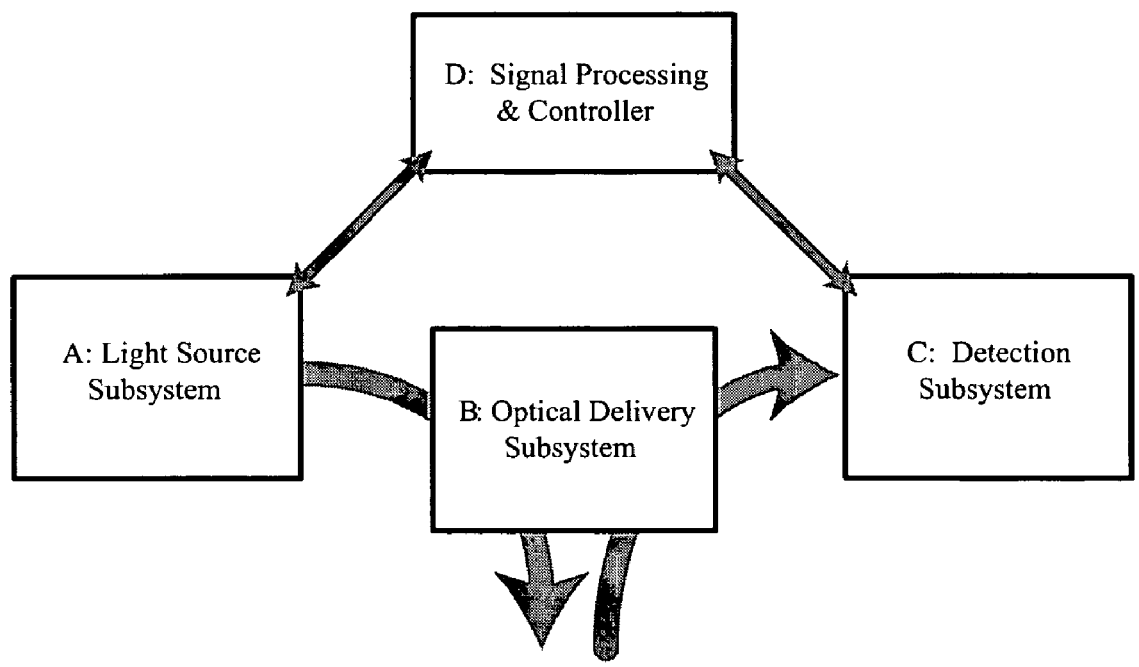
FIG. 11 is a schematic representation of components or sub-systems of an apparatus according to the present invention.

Components or sub-systems of an apparatus to characterize and/or quantify disease state by tissue fluorescence are illustrated in FIG. 11. An illumination subsystem comprises a light source A suitable to illuminate the tissue and thereby electronically excite endogenous chromophores within the tissue. Illumination subsystem includes an optical system B that couples the light produced by the light source A to the tissue and collects the resulting fluorescent light from the tissue sample and couples the collected fluorescence to a detection sub-system C. In the detection subsystem, the fluorescent light is typically converted into an electrical signal. The signal corresponding to the tissue fluorescence is measured and characterized by an analysis or data processing and control system D. The processing/control system can also control or modify the actions of the other sub-systems.

Example I of such a system embodies a high-intensity arc lamp, shutter, monochromator and collimator as the core elements of the light source. The optical-coupling sub-system is comprised of a bifurcated fiber bundle that couples the excitation light to the tissue and collects fluorescence emanating from the tissue. The second leg of the bifurcated bundle couples the collected fluorescent light to the detection sub-system. The detection system contains a monochromator (separate from the monochromator of component A) and a detector such as a photomultiplier. The electrical signal corresponding to the tissue fluorescence is digitized, processed and stored by a computer (Component D). The computer also controls functions of other sub-systems such as the tuning of monochromators and opening closing shutters.

In Example II, the bifurcated fiber-optic bundle of Example I is replaced by a system of lenses and mirrors to convey excitation light from the light source to the tissue and then collect emitted fluorescence from the tissue and relay it to the detection sub-system.

In Example III, the broadband light source of Example I consisting of the high-intensity arc lamp and monochromators is replaced by one or more discrete sources such as LEDs or laser diodes. The LEDs can require suitable optical bandpass filters to produce excitation light that is sufficiently narrow in wavelength. The LEDs or laser diodes can be operated in a continuous wave, modulated or pulsed manner. The output of these sources is coupled to the tissue by an optical sub-system such as the fiber optic bundle of Example I or a collection of mirrors and/or lenses as described for Example II.

In Example IV, the detection system of Example I comprised of a monochromators and single detector is replaced by a spectrograph and a detector array or CCD array.

Figure 12:
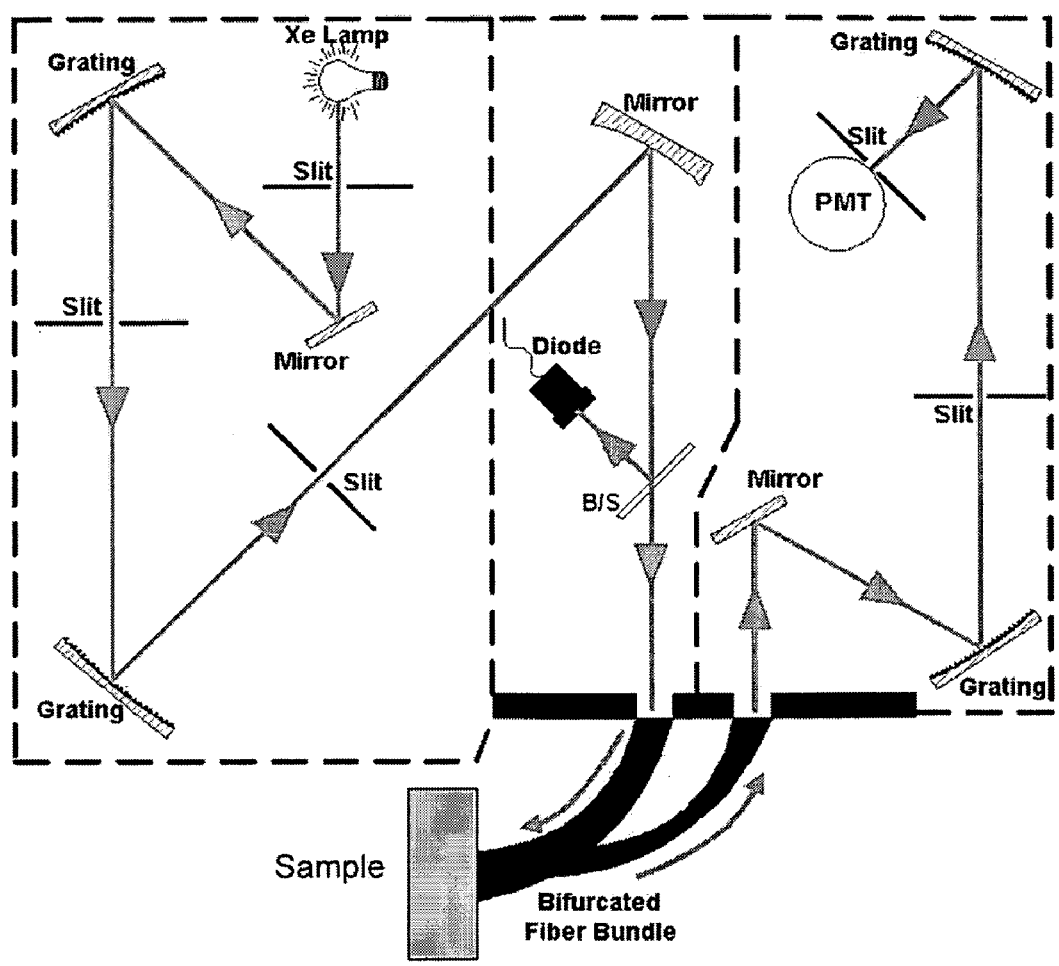
FIG. 12 is a depiction of an example skin fluorimeter.
Figure 13:
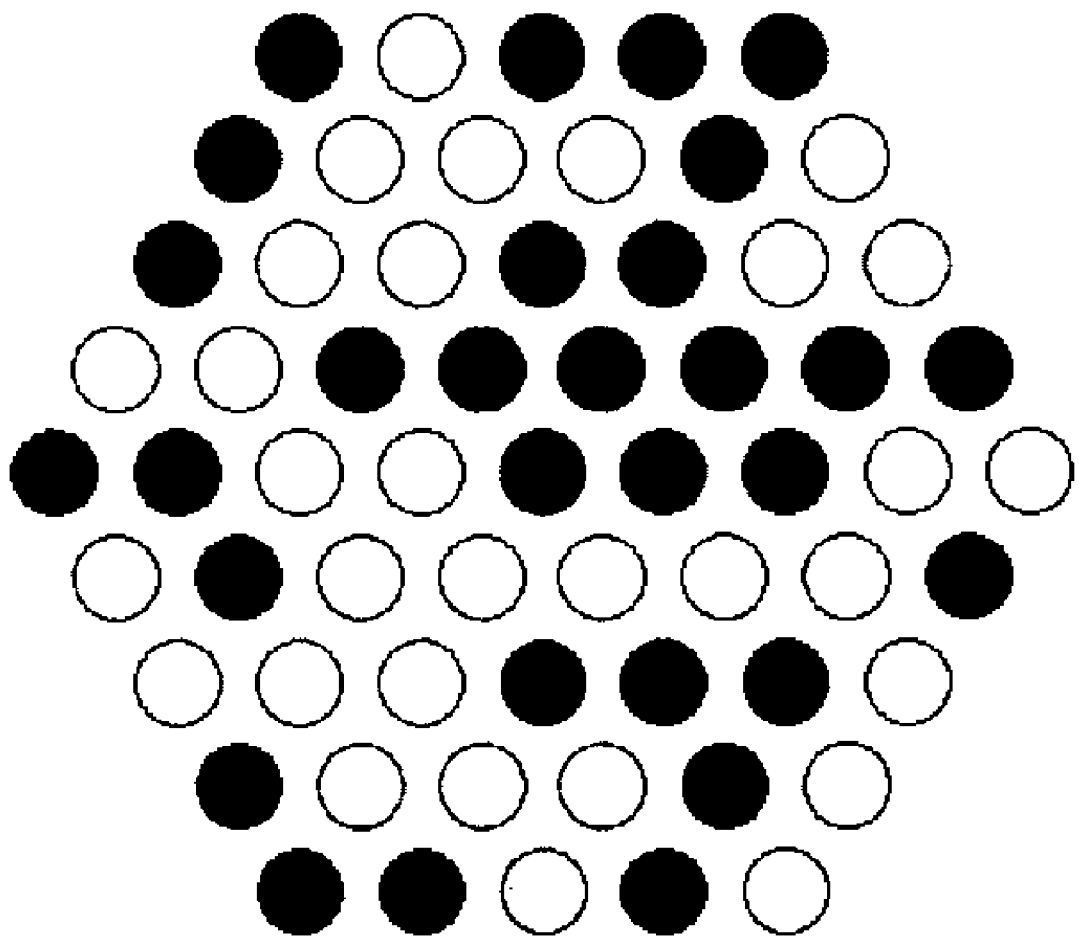
FIG. 13 is a schematic depiction of a portion of an apparatus according to the present invention.
Figure 14:
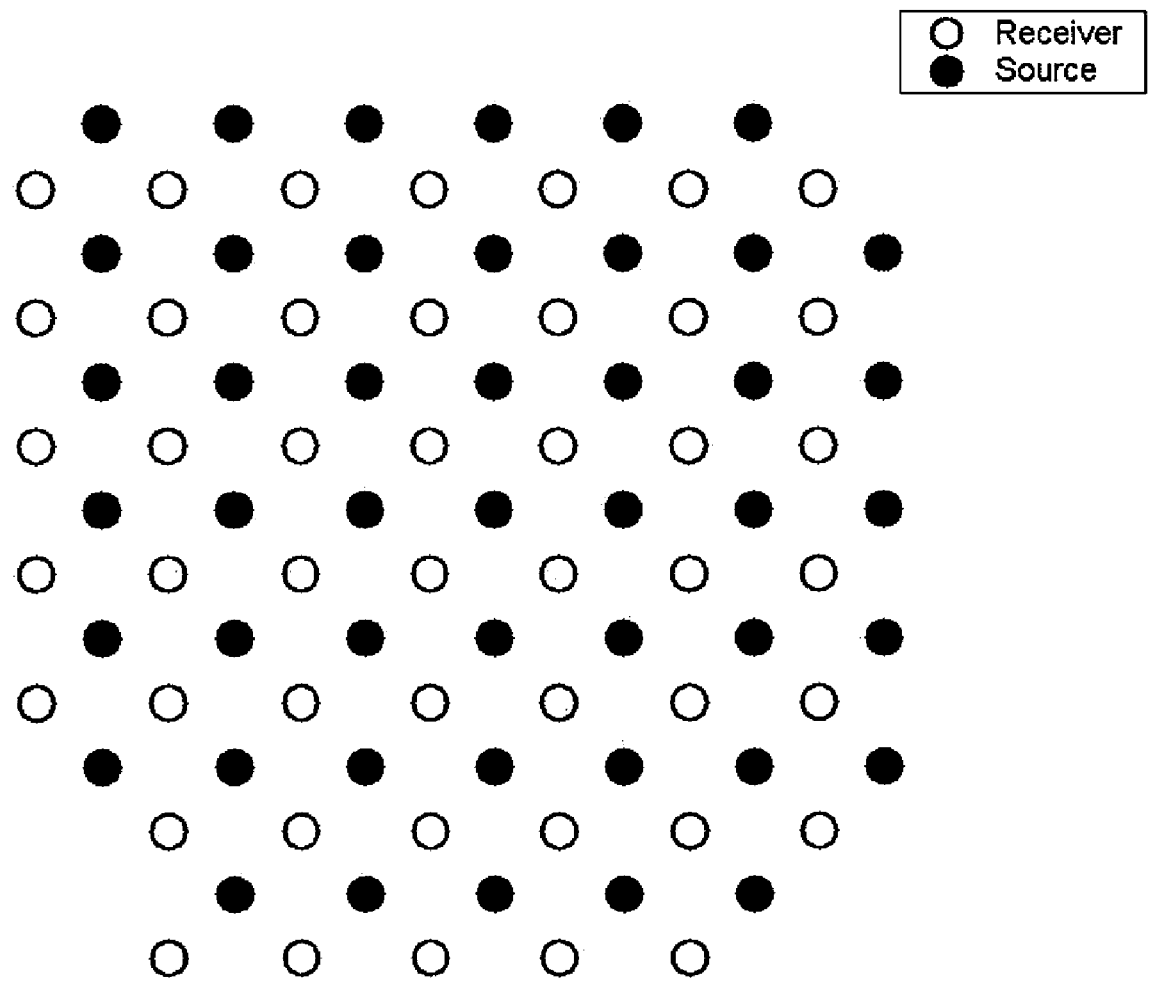
FIG. 14 is a schematic depiction of a portion of an apparatus according to the present invention.
Figure 15:
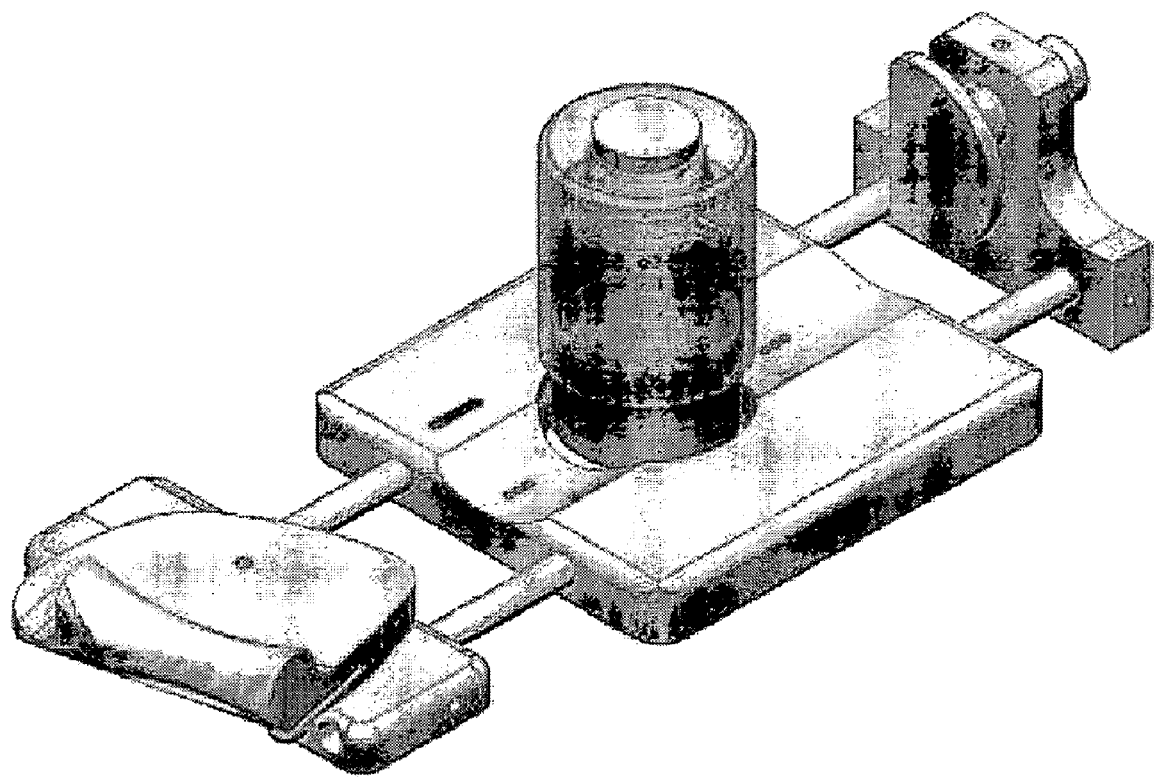
FIG. 15 is an illustration of a tissue interface suitable for use in the present invention.

An example of a skin fluorimeter is presented in FIG. 12. The illumination sub-system consists of a xenon arc lamp coupled to a double monochromator. The spectrally narrow output from the monochromator is coupled into a bifurcated fiber bundle. The fibers in the ferrule contacting the tissue can be arranged randomly, as shown in FIG. 13, or designed with specific source-detector fiber spacing, as illustrated in FIG. 14, can be constructed. An example of a fixture—in this instance, a forearm cradle—to hold the fiber bundle in contact with the skin of the subject is shown in FIG. 15. The cradle provides a means for the subject to comfortably rest their arm while the underside forearm skin is in contact with the delivery/collection end of the fiber bundle. The cradle also facilitates reproducible positioning of the volar forearm site with respect fiber optic bundle. The fluorescence collected by the detector fibers within the bifurcated bundle form the entry slit to a second monochromator of the fluorimeter depicted in FIG. 12. The monochromator filters the incoming fluorescent light and allows a narrow band to fall on the detector, a photomultiplier tube (PMT) or a channel photomultiplier tube. The PMT could be replaced by a sufficiently sensitive silicon avalanche photodiode or regular silicon photodiode. Tunable grating pairs in both the source and detector monochromators allow for the wavelength of each section to be independently tuned. The signal from the PMT is digitized and recorded by a computer that also tunes the gratings, adjusts detector and controls the monochromator shutters.

It can be useful to preferentially collect information from the dermis. FIG. 14 is an illustration of a tissue interface suitable for use in the present invention. The tissue interface comprises a plurality of excitation fibers, in optical communication with a light source and adapted to deliver excitation light to the tissue. It further comprises a plurality of receive fibers, in optical communication with a detector and adapted to receive light emitted from the tissue in response to the excitation light. The receive fibers are spaced apart, and disposed relative to the excitation fibers such that fluorescence information is preferentially collected from the dermis layer of the skin without requiring physical exposure of the dermis.

Figure 16:
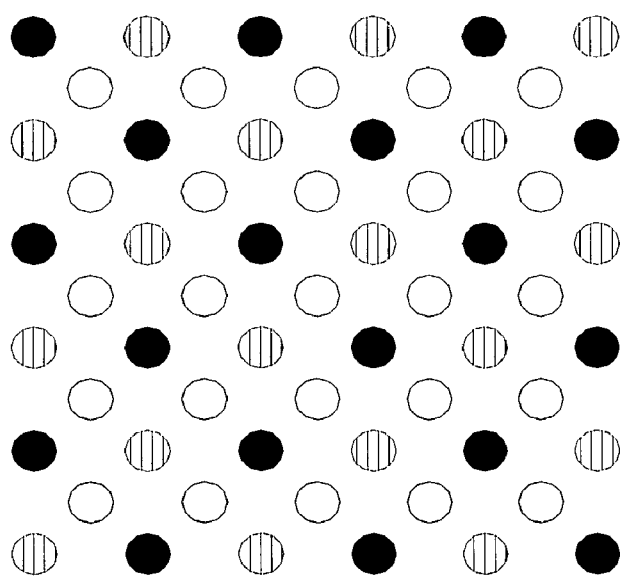
FIG. 16 is a schematic depiction of a multiple-channel fiber optic tissue probe of geometric arrangement.

As discussed previously, it can also be useful to preferentially collect information from the dermis via multiple channels to allow for measurement of optical properties of tissue. FIG. 16 is an illustration of a tissue interface suitable for use in the present invention. The tissue interface comprises a plurality of excitation fibers (shown, for example, as solid circles) in optical communication with a light source and adapted to deliver excitation light to the tissue. It further comprises a plurality of receive fibers (shown, for example, as both open and horizontal line hatched circles) in optical communication with a detector and adapted to receive light emitted from the tissue in response to the excitation light. In the illustration, the open circles comprise a first channel of receive fibers and the hatched circles comprise a second channel of receive fibers. In each of the channels the receive fibers are spaced apart, and disposed relative to the excitation fibers such that fluorescence information is preferentially collected from the dermis layer of the skin without requiring physical exposure of the dermis. Light collected from the skin by each of the receive channels is individually detected either by multiple detectors or through switching between the channels to a single detector.

Figure 18:
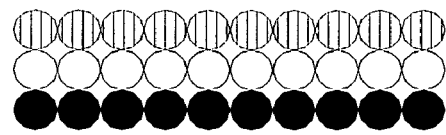
FIG. 18 is a schematic depiction of a multiple-channel fiber optic tissue probe of a linear arrangement.
Figure 17:
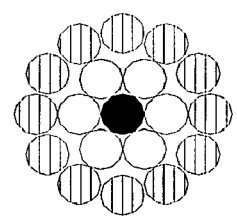
FIG. 17 is a schematic depiction of a multiple-channel fiber optic tissue probe of a circular arrangement.

FIGS. 17 and 18 depict other arrangements of excitation and receive fibers to allow for multiple channels of information to be collected. FIG. 17 shows a circular arrangement of fibers wherein the central (solid circle) fiber delivering excitation light is surrounded by a first channel (open circles) of receive fibers, which is further surrounded by a second channel (hatched circles) of receiver fibers. FIG. 18 shows a linear arrangement of fibers wherein a plurality of excitation fibers (solid circles) are aligned in a row. A first channel of receive fibers (open circles) are positioned in a row parallel to, and some distance from, the excitation row. A second channel of receive fibers (hatched circles) is also positioned in a row parallel to, and some further distance from, the excitation row.

Figure 21:
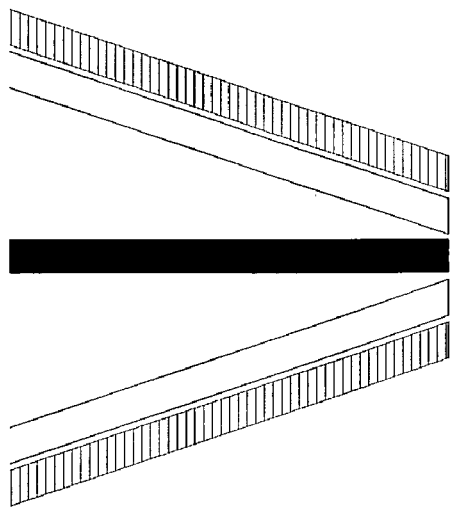
FIG. 21 is a schematic depiction of a sectional view of part of a multiple-channel fiber optic tissue probe of a tilted arrangement.
Figure 20:
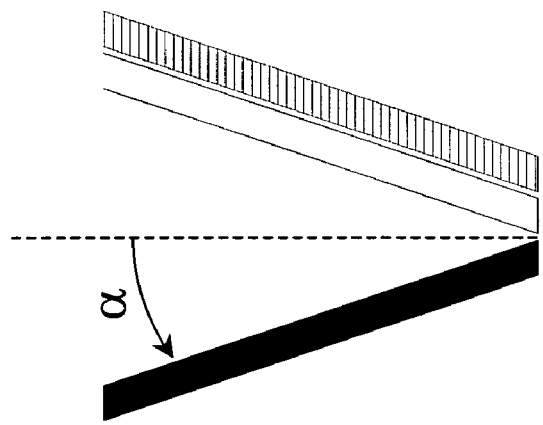
FIG. 20 is a schematic depiction of a sectional view of part of a multiple-channel fiber optic tissue probe of a tilted arrangement.
Figure 19:
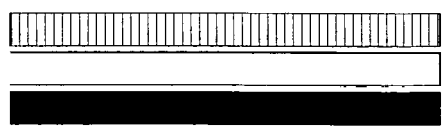
FIG. 19 is a schematic depiction of a sectional view of part of a multiple-channel fiber optic tissue probe of a vertical arrangement.
Figure 22:
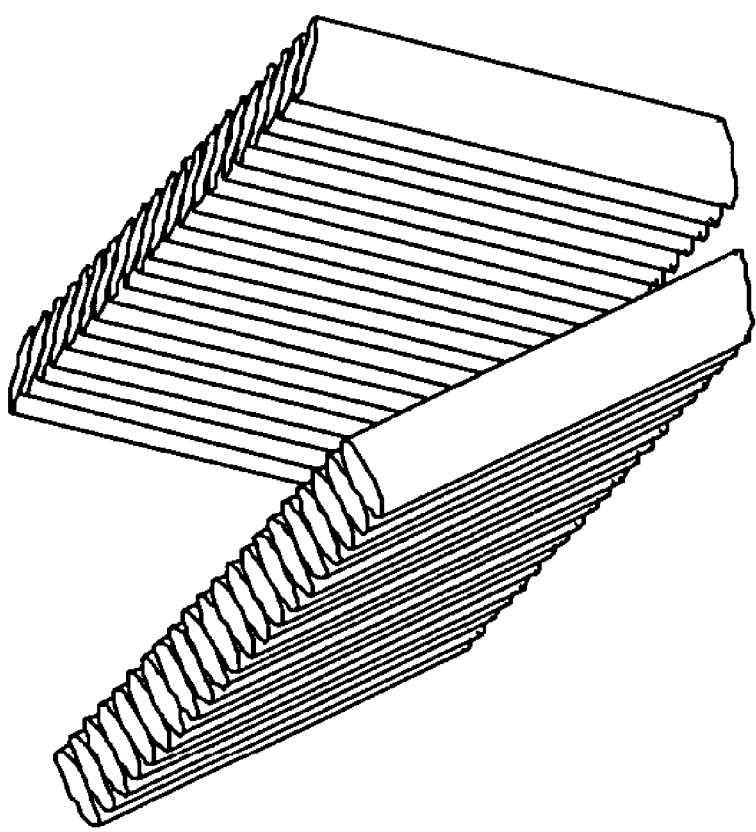
FIG. 22 is a schematic depiction of an isometric view of a fiber optic tissue probe.

FIGS. 19–22 show various views of possible arrangements of a multiple-channel fiber optic tissue probe relative to the sampling surface. FIG. 19 is a schematic depiction of a sectional view of part of a multiple-channel fiber optic tissue probe of a vertical arrangement, wherein the solid fiber can represent an excitation fiber, the open fiber a first receive channel, and the line hatched fiber a second receive channel. In this arrangement the separation between the excitation fiber and first and second receive channels can be chosen so as to proved desired information useful in the determination of tissue optical properties. FIG. 20 is a schematic depiction of a sectional view of part of a multiple-channel fiber optic tissue probe of a tilted arrangement. The tilt angle, $\alpha$, from normal of the excitation fiber may be from 0 to 60 degrees. Likewise, the tilt of the first and second receive channels (open and hatched fibers, respectively) may be tilted in the opposite direction of the excitation fiber from 0 to 60 degrees, and do not necessarily need to be tilted at an equal and opposite amount. FIG. 21 is a schematic depiction of a sectional view of part of a multiple-channel fiber optic tissue probe of a tilted arrangement. Here the first and second receive channels are placed on either side of a central excitation fiber. FIG. 22 is an isometric view showing how several tiled fibers can be arranged in order to increase the light throughput.

Figure 23:
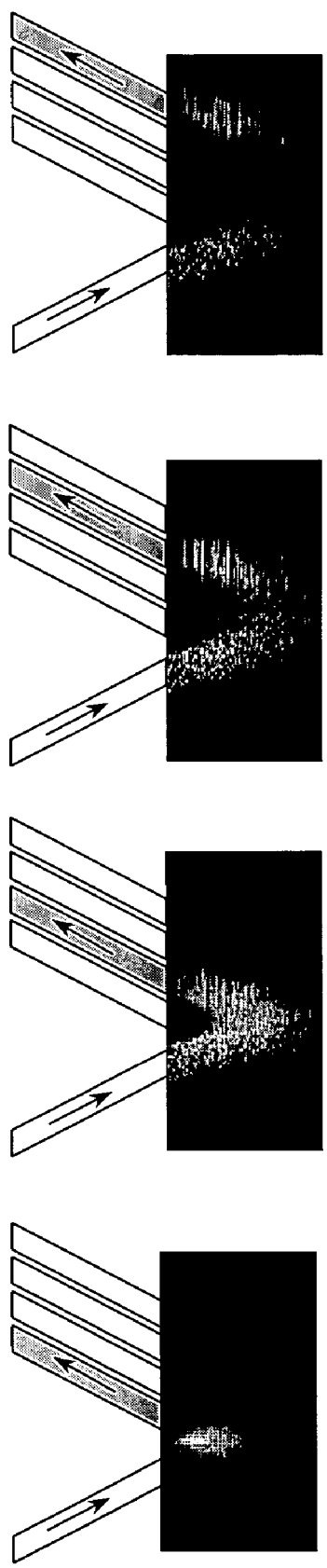
FIG. 23 is an illustration of a multiple-channel fiber optic tissue probe interrogating a tissue volume at various excitation and receiver separations.

FIG. 23 is an illustration of a multiple-channel fiber optic tissue probe interrogating a tissue volume at various excitation and receiver separations. In each of the four illustrations there is a single tilted excitation fiber denoted by an arrow point downward toward a tissue volume shown in black. Opposed to the excitation fiber are four receive fiber channels, each separated a distance away from the excitation fiber. From left to right, the illustrations show the region of tissue interrogated as a function of excitation fiber and receive channel separation. These separate receive channels allow for the preferential collection of information from the dermis which can be useful for the measurement of optical properties of tissue.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

What we claim is:

1. A method of determining a tissue state of the tissue of an individual, comprising:
    a. Illuminating a portion of the tissue of the individual with excitation light;
    b. Detecting light emitted from the tissue by fluorescence of a chemical within the tissue, where the tissue is not the lens of the eye;
    c. Determining the tissue state from the detected light and a model relating fluorescence and a tissue state, wherein detecting light emitted from the tissue comprises:
    d. Determining a tissue reflectance characteristic at an excitation light wavelength;
    e. Detecting light returned from the tissue in response to illumination at the excitation wavelength;
    f. Determining a corrected fluorescence measurement from the detected light and the tissue reflectance characteristic;
    g. And wherein determining a tissue state comprises determining the tissue state from the corrected fluorescence measurement and a model relating fluorescence and tissue state.

2. A method as in claim 1, wherein determining a tissue reflectance characteristic comprises:
    a. illuminating the tissue with reflectance illumination light having the excitation wavelength;
    b. detecting reflectance light having the excitation wavelength reflected from the tissue, using the same detector as used to detect light returned from the tissue; and
    c. establishing a tissue reflectance characteristic from a relationship between the reflectance illumination light and the reflectance light.

3. A method as in claim 1, wherein determining a tissue reflectance characteristic comprises:
    a. illuminating a portion of the tissue with reflectance illumination light having an excitation wavelength;
    b. detecting reflectance light having the excitation wavelength reflected from the portion of the tissue; and
    c. establishing a tissue reflectance characteristic from a relationship between the reflectance illumination light and the reflectance light.

4. A method as in claim 1, further comprising acquiring biologic information relating to the individual, and wherein determining a tissue state comprises determining the tissue state from the corrected fluorescence measurement and a model relating biologic information, fluorescence and tissue state.

5. A method of determining a tissue state of the tissue of an individual, comprising:
    a. Illuminating a portion of the tissue of the individual with excitation light;
    b. Detecting light emitted from the tissue by fluorescence of a chemical within the tissue, where the tissue is not the lens of the eye;
    c. Determining the tissue state from the detected light and a model relating fluorescence and a tissue state wherein detecting light emitted from the tissue comprises:
    d. Determining a tissue reflectance characteristic at a detection wavelength;
    e. Detecting light at the detection wavelength returned from the tissue in response to illumination;
    f. Determining a corrected fluorescence measurement from the detected light and the tissue reflectance characteristic;
    g. And wherein determining a tissue state comprises determining the tissue state from the corrected fluorescence measurement and a model relating fluorescence and tissue state.

6. A method as in claim 5, wherein determining a tissue reflectance characteristic comprises:
    a. illuminating the tissue with reflectance illumination light having a wavelength the same as the detection wavelength;
    b. detecting reflectance light having the detection wavelength reflected from the tissue, using the same detector as used to detect light returned from the tissue; and
    c. establishing a tissue reflectance characteristic from a relationship between the reflectance illumination light and the reflectance light.

7. A method as in claim 5, wherein determining a tissue reflectance characteristic comprises:
    a. illuminating the portion of the tissue with reflectance illumination light having a wavelength the same as the detection wavelength;
    b. detecting reflectance light having the detection wavelength reflected from the portion of the tissue; and
    c. establishing a tissue reflectance characteristic from a relationship between the reflectance illumination light and the reflectance light.

8. A method as in claim 5, further comprising acquiring biologic information relating to the individual, and wherein determining a tissue state comprises determining the tissue state from the corrected fluorescence measurement and a model relating biologic information, fluorescence and tissue state.

9. A method of determining a tissue state of the tissue of an individual, comprising:
    a. Illuminating a portion of the tissue of the individual with excitation light;
    b. Detecting light emitted from the tissue by fluorescence of a chemical within the tissue, where the tissue is not the lens of the eye;

c. Determining the tissue state from the detected light and a model relating fluorescence and a tissue state, wherein detecting light emitted from the tissue comprises:

d. Determining a first tissue reflectance characteristic at an excitation light wavelength;

e. Determining a second tissue reflectance characteristic at a detection wavelength;

f. Detecting light at the detection wavelength returned from the skin in response to illumination at the excitation wavelength;

g. Determining a corrected fluorescence measurement from the detected light and the first and second tissue reflectance characteristics;

h. And wherein determining a tissue state comprises determining the tissue state from the corrected fluorescence measurement and a model relating fluorescence and tissue state.

10. A method of determining a tissue state, other than cancer, of the tissue of an individual, comprising:
  a. Illuminating a portion of the tissue of the individual with excitation light;
  b. Detecting light emitted from the tissue by fluorescence of a chemical within the tissue, where the tissue is not the lens of the eye;
  c. Determining the tissue state from the detected light and a model relating fluorescence and a tissue state;
  further comprising acquiring biologic information relating to the individual, and wherein determining a tissue state comprises determining the tissue state from the information, the detected light, and a model relating biologic information, fluorescence and tissue state, wherein the biologic information comprises gender of the individual, height of the individual, weight of the individual, waist circumference of the individual, history of disease in the individuals family, ethnicity, skin melanin content, smoking history of the individual, or a combination thereof.

11. A method as in claim 10, wherein the excitation light has a wavelength in the range from 280 nm to 500 nm.

12. A method as in claim 11, wherein the excitation light has a wavelength in the range from 315 nm to 500 nm.

13. A method as in claim 10, wherein the excitation light has a first wavelength at a first time, and a second wavelength, different from the first wavelength, at a second time.

14. A method as in claim 10, wherein detecting light emitted from the tissue comprises detecting light at a wavelength greater than the excitation light wavelength.

15. A method as in claim 10, wherein detecting light emitted from the tissue comprises detecting light at a wavelength between 280 nm and 850 nm.

16. A method as in claim 10, wherein detecting light emitted from the tissue comprises detecting light at each of a plurality of wavelengths.

17. A method as in claim 16, wherein the excitation light has a single wavelength, and wherein detecting light emitted from the tissue comprises detecting light at a plurality of wavelengths.

18. A method as in claim 10, wherein the excitation light wavelength varies with time, and wherein detecting light emitted from the tissue comprises detecting light at a first wavelength.

19. A method as in claim 10, wherein the tissue comprises the skin of the individual.

20. A method as in claim 10, wherein the model is determined according to:
  a. For each of a plurality of subjects:
    i. Determining a fluorescence property of a portion of the tissue of the subject;
    ii. Determining a tissue state of the subject;
  b. Applying a multivariate method to the plurality of fluorescence property determinations and associated tissue state determinations to generate a model relating fluorescence property to a tissue state.

21. A method according to claim 10, wherein the tissue state comprises the presence of glycation end-products, the concentration of glycation end-products, the change in the concentration of glycation end-products, the presence of glycated collagen, the concentration of glycated collagen, the change in the concentration of glycated collagen, the disease state of the individual, or a combination thereof.

22. A method of determining a tissue state in an individual, comprising:
  a. Establishing an interface between an optical system and a portion of the skin of the individual;
  b. Determining a relationship of illumination light at an excitation wavelength and the response of the skin at a detection wavelength for each of a plurality of pairings of excitation wavelength and detection wavelength;
  c. Determining a tissue reflectance property of the skin at each of the illumination wavelengths and at each of the detection wavelengths;
  d. Determining a measure of the intrinsic fluorescence of the skin from the relationships of illumination light and detected light and the tissue reflectance properties;
  e. Determining the tissue state of the individual from the intrinsic fluorescence using a model relating intrinsic fluorescence and tissue state.

23. A method as in claim 22, further comprising acquiring biologic information relating to the subject, and wherein determining a tissue state comprises determining the tissue state from the biologic information, the detected light, and a model relating biologic information, fluorescence and tissue state.

24. A method as in claim 23, wherein the biologic information comprises information from Raman spectroscopic investigation of the subject.

25. A method as in claim 23, wherein the biologic information comprises gender of the individual, height of the individual, weight of the individual, waist circumference of the individual, history of disease in the individual's family, ethnicity, skin melanin content, blood HDL cholesterol level of the subject, blood LDL cholesterol level of the subject, blood triglycerides level of the subject, laser-Doppler information from the subject's tissue, smoking history of the individual, or a combination thereof.

26. A method of determining a model relating fluorescence and tissue state, where "tissue state" is any of (i) a disease state based on long-term changes (greater than one month duration) in tissue, (ii) a measure of chemical change based on long-term (greater than one month duration) glycemic control, (iii) a measure of glycation end-products in tissue, and (iv) a combination of the above, comprising:
  a. For each of a plurality of subjects:
    i. Determining a fluorescence property of a portion of the tissue of the subject, where the tissue is not the lens of the eye, by illuminating the portion of the tissue with excitation light; determining a tissue reflectance characteristic at the excitation light wavelength, detecting light returned from the tissue in response to illumination at the excitation wavelength, determining a corrected fluorescence measurement from the detected light and the tissue reflectance characteristic;
  ii. Determining a tissue state of the subject;
  b. Applying a multivariate method to the plurality of corrected fluorescence measurements and associated tissue state determinations to generate a model relating fluorescence property to tissue state.

27. A method as in claim 26, wherein determining a fluorescence property comprises determining an intrinsic fluorescence of the portion of the tissue.

28. A method as in claim 26, wherein determining a fluorescence property comprises determining an intrinsic fluorescence of the portion of the tissue at each of a plurality of detection wavelengths responsive to excitation light having an excitation wavelength.

29. A method as in claim 26, wherein determining a fluorescence property comprises determining an intrinsic fluorescence of the portion of the tissue at a detection wavelength responsive to excitation light at a plurality of excitation wavelengths.

30. A method as in claim 26, wherein determining a fluorescence property comprises determining an intrinsic fluorescence of the portion of the tissue at pairings of a plurality of detection wavelengths and a plurality of excitation wavelengths.

31. A method as in claim 26, wherein determining a fluorescence property of a portion of the tissue of the subject comprises:
  a. Illuminating the portion of the tissue of the individual with excitation light;
  b. Detecting light emitted from the tissue by fluorescence of a chemical within the tissue.

32. A method as in claim 26, wherein determining a tissue state comprises at least one of:
  a. Evaluating the subject according to an OGTT;
  b. Evaluating the subject according to an FPG;
  c. Evaluating the subject according to an HbA1c test;
  f. Determining a previous disease state determination from disease state declared by the subject;
  g. Determining a level of glycation endproducts in the tissue of the subject.

33. A method as in claim 26, wherein applying a multivariate method comprises applying a multivariate model constructed according to the Partial Least Squares, Principal Components Regression, Principal Components Analysis, Classical Least Squares, Multiple Linear Regression, Ridge Regression algorithms, Linear Discriminant algorithms, Quadratic Discriminant algorithms, Logistic Regression algorithms, or a combination thereof.

34. A method as in claim 26, wherein the portion of the tissue comprises the skin of the subject.

35. A method of determining a model relating fluorescence and tissue state, comprising:
  a. For each of a plurality of subjects:
    i. Determining a fluorescence property of a portion of the tissue of the subject, where the tissue is not the lens of the eye;
    ii. Determining a tissue state of the subject;
  b. Applying a multivariate method to the plurality of fluorescence property determinations and associated tissue state determinations to generate a model relating fluorescence property to tissue state; wherein determining a fluorescence property of a portion of the tissue of the subject comprises:
  c. Illuminating the portion of the tissue of the individual with excitation light;
  d. Detecting light emitted from the tissue by fluorescence of a chemical within the tissue, wherein detecting light emitted from the tissue comprises:
  e. Determining a tissue reflectance characteristic at an excitation light wavelength;
  f. Detecting light returned from the tissue in response to illumination at the excitation wavelength;
  g. Determining a corrected fluorescence measurement from the detected light and the tissue reflectance characteristic.

36. A method of determining a model relating fluorescence and tissue state, comprising:
  a. For each of a plurality of subjects:
    i. Determining a fluorescence property of a portion of the tissue of the subject, where the tissue is not the lens of the eye;
    ii. Determining a tissue state of the subject;
  b. Applying a multivariate method to the plurality of fluorescence property determinations and associated tissue state determinations to generate a model relating fluorescence properly to tissue state; wherein determining a fluorescence property of a portion of the tissue of the subject comprises:
  c. Illuminating the portion of the tissue of the individual with excitation light;
  d. Detecting light emitted from the tissue by fluorescence of a chemical within the tissue, wherein detecting light emitted from the tissue comprises:
  e. Determining a tissue reflectance characteristic at a detection wavelength;
  f. Detecting light at the detection wavelength returned from the tissue in response to illumination;
  g. Determining a corrected fluorescence measurement from the detected light and the tissue reflectance characteristic.

37. A method of determining a model relating fluorescence and tissue state, comprising:
  a. For each of a plurality of subjects:
    i. Determining a fluorescence property of a portion of the tissue of the subject, where the tissue is not the lens of the eye;
    ii. Determining a tissue state of the subject;
  b. Applying a multivariate method to the plurality of fluorescence property determinations and associated tissue state determinations to generate a model relating fluorescence property to tissue state; wherein determining a fluorescence property of a portion of the tissue of the subject comprises:
  c. Illuminating the portion of the tissue of the individual with excitation light;
  d. Detecting light emitted from the tissue by fluorescence of a chemical within the tissue, wherein detecting light emitted from the tissue comprises:
  e. Determining a first tissue reflectance characteristic at an excitation light wavelength;
  f. Determining a second tissue reflectance characteristic at a detection wavelength;
  g. Detecting light at the detection wavelength returned from the skin in response to illumination at the excitation wavelength;
  h. Determining a corrected fluorescence measurement from the detected light and the first and second tissue reflectance characteristics.

38. An apparatus for the determination of a tissue state, other than cancer, in an individual, where "tissue state" is any of (i) a disease state based on long-term changes (greater than one month duration) in tissue, (ii) a measure of chemical change based on long-term (greater than one month duration) glycemic control, (iii) a measure of glycation end-products in tissue, and (iv) a combination of the above, comprising:
   a. An illumination subsystem;
   b. A detection subsystem;
   c. An analysis subsystem, comprising a model relating fluorescence property of the skin and biologic information an individual to tissue state, wherein biologic information comprises gender of the individual, height of the individual, weight of the individual, waist circumference of the individual, history of disease in the individual's family, ethnicity, skin melanin content, smoking history of the individual, or a combination thereof.

39. An apparatus as in claim 38, wherein the model is determined according to:
   a. For each of a plurality of subjects:
      i. Determining a fluorescence property of a portion of the tissue of the subject;
      ii. Determining a tissue state of the subject;
   b. Applying a multivariate method to the plurality of fluorescence property determinations and associated tissue state determinations to generate a model relating fluorescence property to tissue state.

40. A method of determining a tissue state in an individual, where "tissue state" is any of (i) a disease state based on long-term changes (greater than one month duration) in tissue, (ii) a measure of chemical change based on long-term (greater than one month duration) glycemic control, (iii) a measure of glycation end-products in tissue, and (iv) a combination of the above, comprising:
   a. Determining a fluorescence property of a portion of the skin of the individual by illuminating the portion of the skin with excitation light; determining a skin reflectance characteristic at the excitation light wavelength, detecting light returned from the skin in response to illumination at the excitation wavelength, determining a corrected fluorescence measurement from the detected light and the skin reflectance characteristic;
   b. Using a multivariate method to determine a tissue state of the individual from the corrected fluorescence measurement.

41. A method according to claim 40, wherein:
   a. The fluorescence property comprises the intrinsic fluorescence of the portion of the skin;
   b. The tissue state comprises the concentration of glycation end-products;
   c. Using a multivariate method comprises applying a multivariate model relating intrinsic fluorescence of skin to the concentration of glycation end-products.

42. A method according to claim 40, wherein determining a fluorescence property comprises determining the tissue's response to amplitude-modulated excitation light, a short pulse of excitation light, or polarized excitation light, or a combination thereof.

43. A method according to claim 40, wherein determining a fluorescence property comprises using confocal detection or optical coherence tomography to discriminate the tissue depth from which the fluorescence property originates.

44. A method according to claim 40, wherein determining a fluorescence property comprises using raster scanning or imaging optics to obtain information regarding the spatial distribution of the fluorescence property.

* * * * *